United States Patent
Czerney et al.

(10) Patent No.: US 7,553,869 B2
(45) Date of Patent: Jun. 30, 2009

(54) PROTEIN PROBE COMPOUNDS, COMPOSITIONS, AND METHODS

(75) Inventors: Peter T. Czerney, Weimar (DE); Surbhi Desai, Rockford, IL (US); Frank G. Lehmann, Jena (DE); Zakir S. Murtaza, Vernon Hills, IL (US); Bernd G. Schweder, Jena (DE); Matthias S. Wenzel, Jena (DE); Brian David Wolf, Machesney Park, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 190 days.

(21) Appl. No.: 11/460,700

(22) Filed: Jul. 28, 2006

(65) Prior Publication Data

US 2008/0026478 A1  Jan. 31, 2008

(51) Int. Cl.
  *A01N 43/16* (2006.01)
  *A61K 31/35* (2006.01)
  *C07D 311/02* (2006.01)
(52) U.S. Cl. ...................... 514/456; 549/285
(58) Field of Classification Search ................ 549/285; 514/456
  See application file for complete search history.

(56) References Cited

U.S. PATENT DOCUMENTS

2002/0115862 A1  8/2002 Czerney et al.
2003/0165942 A1  9/2003 Czerney et al.
2004/0260093 A1  12/2004 Czerney et al.
2006/0166368 A1  7/2006 Berkelman

FOREIGN PATENT DOCUMENTS

| EP | 1318177 A2 | 6/2003 |
| EP | 1535969 A2 | 6/2006 |
| JP | 2003086257 | * 3/2003 |
| WO | WO00/53678 | 9/2000 |
| WO | WO01/90253 A1 | 11/2001 |
| WO | WO2006/025887 A2 | 3/2006 |

OTHER PUBLICATIONS

European Patent Office, International Search Report and Written Opinion of PCT/US2006/029603, Mailed Jun. 22, 2007.

* cited by examiner

*Primary Examiner*—D. Margaret Seaman
*Assistant Examiner*—Niloofar Rahmani
(74) *Attorney, Agent, or Firm*—Thompson Hine LLP; Beverly A. Lyman

(57) ABSTRACT

Coumarine/chinolone and Martina-type compounds, compositions, and method of using the compounds and compositions for protein detection, assay, quantitation, etc. are disclosed. The composition, also referred to as a dye, has enhanced sensitivity over commercially available protein stains, and may be used to stain proteins in solution, proteins separated on gels, proteins transferred to solid supports, etc.

13 Claims, 12 Drawing Sheets

PROTEIN PROBE COMPOUNDS, COMPOSITIONS, AND METHODS

FIELD OF THE INVENTION

Compounds and dye compositions and methods for detecting and quantitating biomolecules such as proteins.

BACKGROUND

Protein detection and quantitation are important bioanalytical tools. Amounts of proteins in solutions, gels, etc. are determined by their interaction with compounds that are fluorescent dyes. Examples include Albumin-Blue which is based on a cyanin structure (Wolfbeis et al., U.S. Pat. No. 5,182,214), merocyanines (Haugland et al., U.S. Pat. No. 5,616,502), and SYPRO Ruby which is derived from a metal-ligand complex (Haugland et al., Handbook of Fluorescent Probes and Research Products, 9th Edition, also http://www.probes.com). The adsorption of the compounds to the surface of proteins leads, among other effects, to rigidization of the molecular structure of the chromophore, resulting in a drastic increase of the quantum yield. Hydrogen bond formation and shielding against dissolved oxygen quenching of the emission also increase the emission signal.

Czerney et al. (e.g., EP 1318177, EP 1535969, US 2004/260093, DE 10159078) have described reactive labels, inter alia, on the basis of coumarin- and chinolone-based dyes which are suited for the covalent labelling of biomolecules. One example is 4-hydroxysubstituted coumarin dyes, which bear a reactive function.

Other dyes and properties are desirable

DETAILED DESCRIPTION

Figure 1:
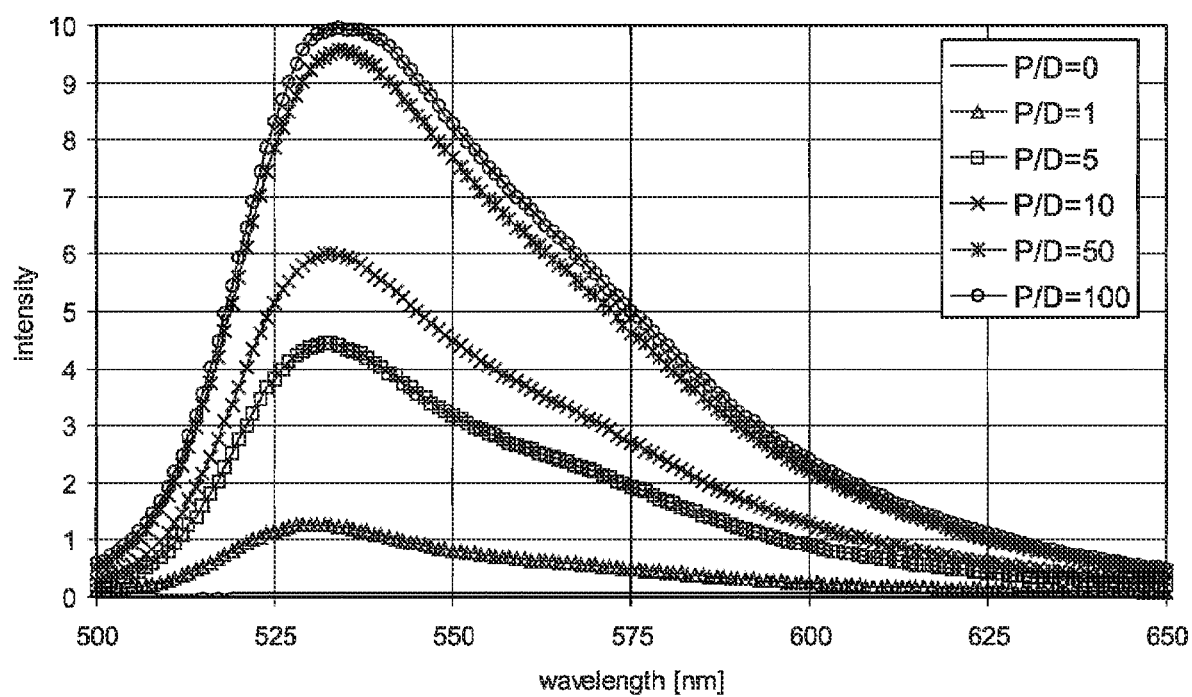
FIG. 1 shows expected fluorescence of solutions having different protein:dye ratios.

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

Compounds, biocompatible compositions of the compounds also referred to herein as dyes, and uses of the compounds and dyes are disclosed. The compounds bind a biomolecule, such as a protein, by non-covalent interactions, and this binding is accompanied by changes in the optical properties of the compounds. Compound binding may occur in vitro and/or in vivo. Binding occurs by non-covalent bonds (e.g., electrostatic, ionic, hydrogen, van der Waals forces, etc.) because the compounds lack a reactive chemical group (e.g., the compounds lack a carboxy alkyl ester, amine, etc.).

A method for detecting and quantitating poly(amino) acids, peptides, and/or proteins using these dyes is disclosed. Unless otherwise disclosed, reference to protein detection includes detection of poly(amino) acids and/or peptides. The proteins may be in solution or on a support such as a membrane, gel, etc. In one embodiment, dyes are used to bind proteins in solution, e.g., aqueous buffer. In one embodiment, changes in fluorescence properties of 4-substituted coumarin- or chinolone-based dyes, in the presence of proteins, are disclosed.

Methods include proteins staining, quantitation, assay, detection, etc. Methods encompass any qualitative and/or quantitative determination of the presence, characterization, function, etc. of one or more proteins. Methods also include diagnostics, bioanalytics, etc.

The method lacks heavy metal-containing reagents used in conventional metal-ligand complex protein determination, and hence lacks attendant disposal, toxicity, and other problems using such heavy metal-containing reagents. The dyes are compatible with argon-, helium/neon-, and diode laser techniques used in bioanalytics and medical diagnostics.

In one embodiment, the method permits enhanced staining of proteins that contain specific functional groups. For example, one embodiment of the method permits enhanced staining of glycoproteins, and another embodiment permits enhanced staining of phosphoproteins.

In one embodiment, compounds referred to herein as coumarine/chinolone derivatives, which are covalently connected via one or more vinylene units with benzopyrylium compound type dyes are disclosed. Coumarine/chinolone type Type I and II dyes absorb electromagnetic radiation in the near infrared (NIR) and red region of the electromagnetic spectrum. These NIR dyes have excitation maxima in the region between 480 nm and 800 nm, and emission maxima between 500 nm and 820 nm.

In one embodiment, coumarine/chinolone dyes of the general formula type I

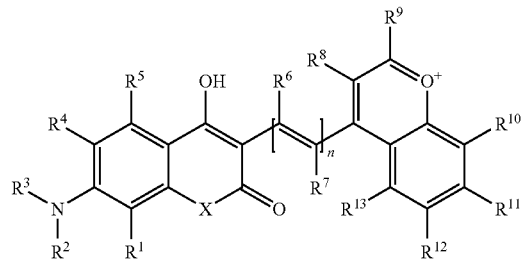

and Type II

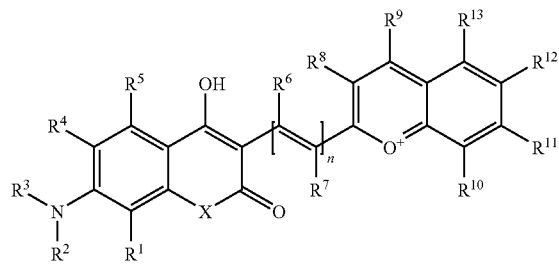

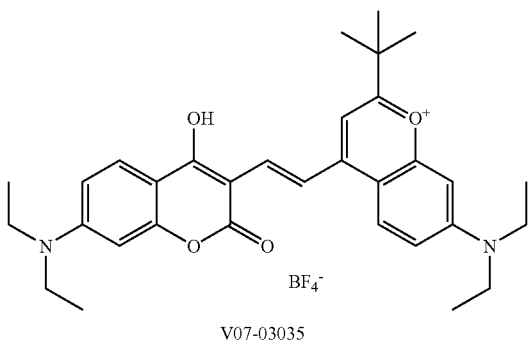

V07-03035

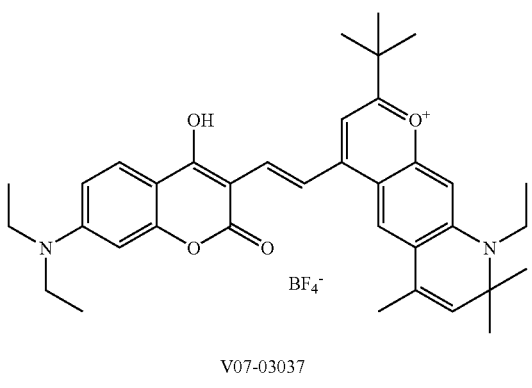

V07-03037

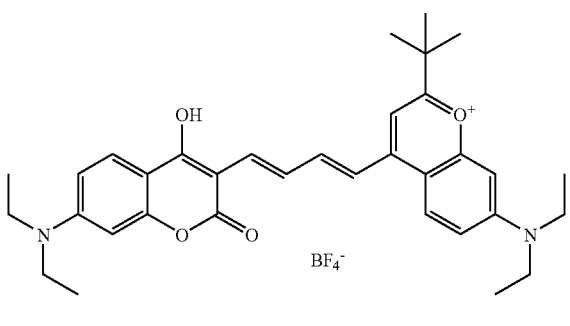

V07-05146

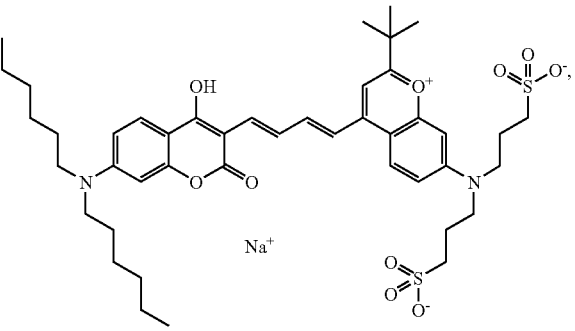

V07-05146 are disclosed. In coumarine/chinolond dyes of the general formula Type I and Type II, $R^1$ to $R^{10}$, $R^{12}$, and $R^{13}$ are the same or different and are selected from the group consisting of hydrogen, chlorine, bromine, sulfonate, alkyl, ter.-alkyl, aryl, carboxyaryl, heteroaryl, cycloalkyl, heterocycloalkyl, cyano, hydroxy, alkyloxy, alkylmercapto, aryloxy, arylmercapto, heteroaryloxy, heteroarylmercapto, hydroxyalkyl, carboxyalkyl, sulfoalkyl and cyanoalkyl-residues, or are N-mono- or N.N-di-alkylsubstituted amino or cyclic amino functions, $R^{11}$ is $OR^{14}$ or $NR^{15}R^{16}$ whereby $R^{14}$-$R^{16}$ can have the same or different functionalities equal to $R^1$-$R^{10}$, $R^1$ and $R^2$, and/or $R^2$ and $R^3$, and/or $R^3$ and $R^4$, and/or $R^7$ and $R^8$, and/or $R^{10}$ and $R^{14}$, and/or $R^{12}$ and $R^{14}$, and/or $R^{10}$ and $R^{15}$, and/or $R^{12}$ and $R^{16}$ and/or $R^{15}$ and $R^{16}$, can form further substituted aliphatic or aromatic ring systems, $R^6$ and $R^7$ are the same or different, whereby aliphatic bridges between neighboring or in 1,3-position to each other located $R^6$— or $R^7$-substituents are possible if n=2, 3, or 4, X is selected from the group consisting of O, S, $NR^{17}$, and $CR^{18}R^{19}$, whereby $R^{17}$-$R^{19}$ can have the same or different functionalities equal to $R^1$-$R^{10}$, and n=0 to 4.

Specific embodiments of the general Type I structure include the following compounds designated as V07-03035, V07-03037, V07-05146, V07-05176, V07-05170, and V02-06006, a follows:

which is a modified form of V07-05146 containing a longer alkyl chain and a sulfoalkyl group

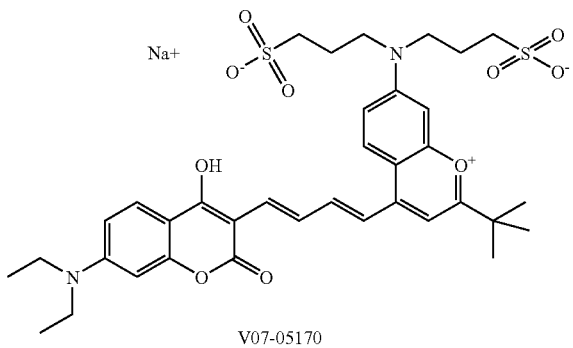

V07-05170

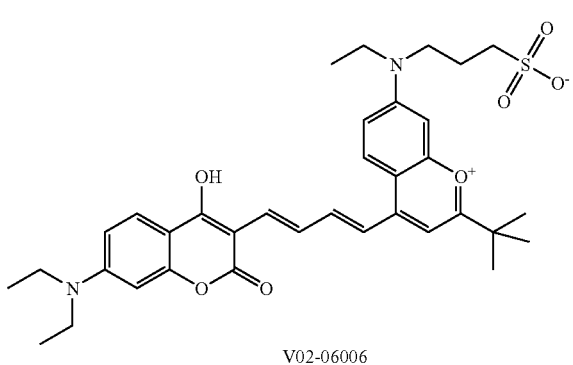

V02-06006

Each of V07-03035, V07-03037, V07-05146, V07-05176, V07-05170, and V02-06006 has absorbance maxima in the NIR region of the electromagnetic spectrum. V07-05176 is a hydroxyl-coumarine derivative of V07-06050 (Martina Red), which is subsequently disclosed.

Specific embodiments of the general Type II structure include the following compounds designated as V07-05143, and V07-03034, as follows:

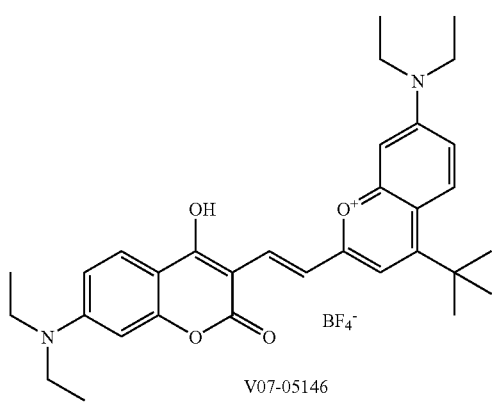

V07-05146

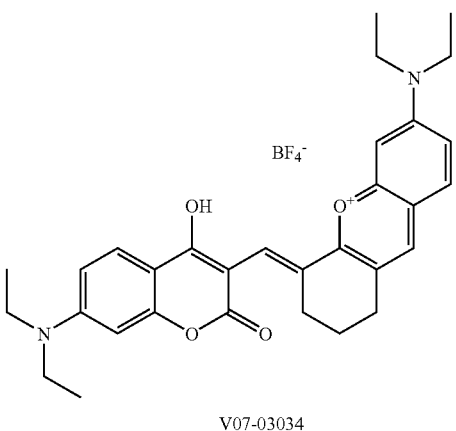

V07-03034

Selected characteristics of the coumarine/chinolone type dyes are presented in Table 1.

TABLE 1

|  | MW g/mol | Molar Absorbance ε mol$^{-1}$ cm$^{-1}$ in MeOH | Absorption Max. $\lambda_{abs}$ nm in MeOH | Emission Max. $\lambda_{em}$ nm in Me |
|---|---|---|---|---|
| V07-05146 | 628.55 | 90,000 | 683 | 715 |
| V07-05176 | 863.09 | 140,000 | 684 | 723 |
| V02-06006 | 634.80 | 75,000 | 687 | 712 |
| V07-05170 | 750.87 | 90,000 | 682 | 717 |
| V07-03035 | 602.48 | 111,000 | 590 | 620 |
| V07-03037 | 654.56 | 160,000 | 606 | 638 |
| V07-05143 | 602.48 | 95,000 | 636 | 666 |
| V07-03034 | 599.09 | 110,000 | 680 | 707 |

When V07-05146 was formulated as a dye, protein detection sensitivity was 1 ng with low background.

When V07-05176 was formulated as a dye, in one embodiment, protein detection sensitivity was less than or equal to 0.5 ng with low background, and in another embodiment, protein detection sensitivity was in the high pictogram range.

When V02-06006 was formulated as a dye, protein detection sensitivity was less than or equal to about 1 ng with low background.

When V07-05170 was formulated as a dye, in one embodiment, protein detection sensitivity was less than 2 ng with low background, and in another embodiment, protein detection sensitivity was less than or equal to 1.98 ng. In phosphate buffered saline, the dye did not demonstrate an emission spectrum except in the presence of a protein.

In one embodiment, compounds V02-06006 and V07-05176 are combined with at least one excipient for form a dye. Protein detection sensitivity was 0.25 ng.

Synthesis of Type I coumarine/chinolone compounds was according to the following general method; each of the cited references are expressly incorporated by reference herein:

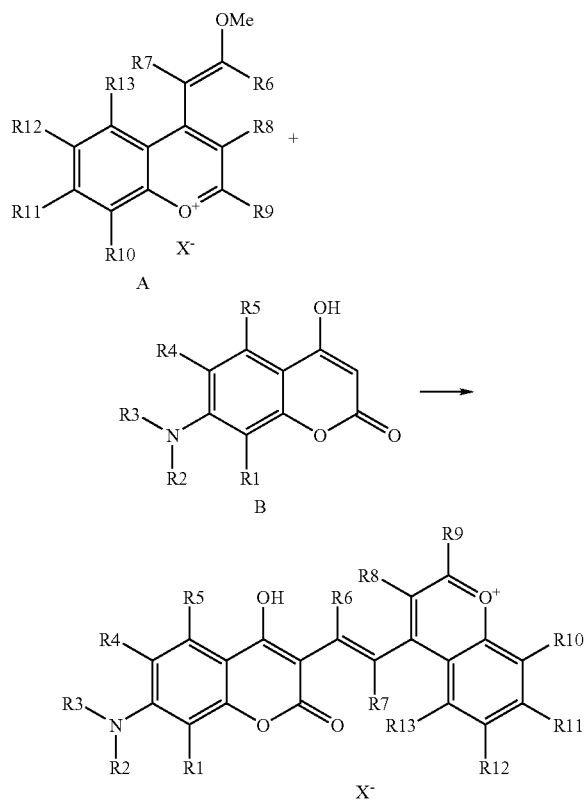

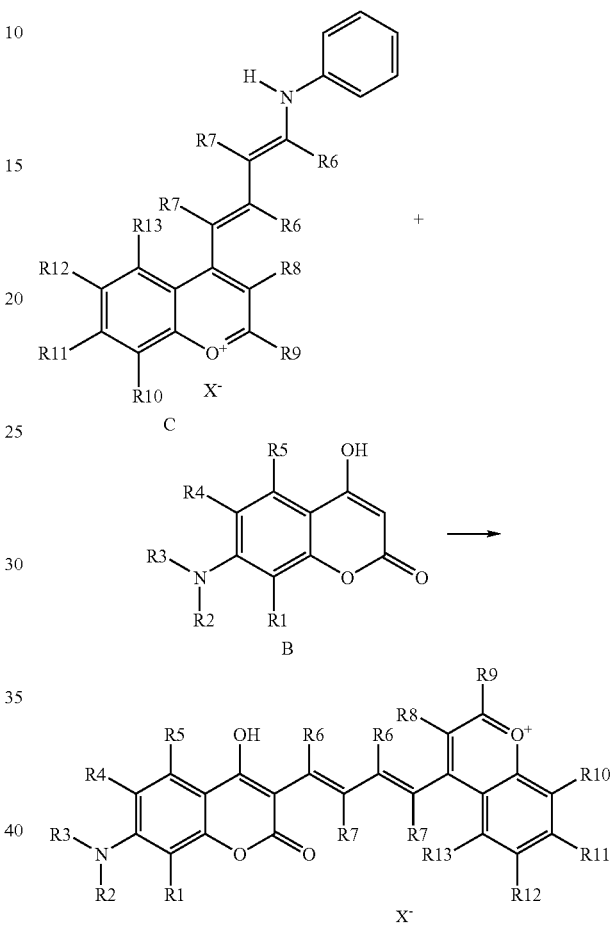

A solution of a 4-((E)-2-methoxy-vinyl)-chromenylium compound A (0.5 mmol) (Dyes and Pigments 17, 153 (1991)) and 7-dialkylamino-4-hydroxy-chromen-2-one B (0.5 mml) (J. Heterocycl. Chem. 17, 225 (1980)) in 8 ml acetic acid anhydride/pyridine mixture was refluxed for four hours. After cooling, diethylether was added and the ether solution was removed. The remaining precipitate was purified by column-chromatography.

Synthesis of specific Type II coumarine/chinolone compounds was as follows; each of the cited references are expressly incorporated by reference herein:

V07-03035

Synthesis of 2-tert-butyl-7-diethylamino-4-[(E)-2-(7-diethylamino-4-hydroxy-2-oxo-2H-chromen-3-yl)-vinyl]-chromenylium tetrafluoroborate (V07-03035) from 4-((E)-2-methoxy-vinyl)-7-diethylamino-2-tert-butyl-chromenylium tetrafluoroborate and 7-diethylamino-4-hydroxy-chromen-2-one. Purification was on silica with toluene/ethanol gradient. Yield: 360 mg dark powder $C_{32}H_{39}N_2O_4{}^+BF_4{}^-$ (602.48 g/mol); MS (ES+) [m/z]: 515 [M$^+$]

$\lambda_{abs}$: 590 nm; $\lambda_{em}$: 620 nm; $\epsilon$: 110.000 mol$^{-1}$ cm$^{-1}$ in MeOH

V07-03037

Synthesis of 2-tert-butyl-4-[(E)-2-(7-diethylamino-4-hydroxy-2-oxo-2H-chromen-3-yl)-vinyl]-8-ethyl-5,7,7-trimethyl-7,8-dihydro-1-oxonia-8-aza-anthracene tetrafluoroborate (V07-03037) from 2-tert-Butyl-8-ethyl-4-((E)-2-methoxy-vinyl)-5,7,7-trimethyl-7,8-dihydro-1-oxonia-8-aza-anthracene tetrafluoroborate and 7-diethylamino-4-hydroxy-chromen-2-one. Purification was on silica with toluene/ethanol gradient. Yield: 190 mg dark powder $C_{36}H_{43}N_2O_4{}^+BF_4{}^-$ (654.56 g/mol); MS (ES+) [m/z]: 567 [M$^+$]

$\lambda_{abs}$: 606 nm; $\lambda_{em}$: 638 nm; $\epsilon$: 160.000 mol$^{-1}$ cm$^{-1}$ in MeOH Synthesis of another type I coumarine/chinolone compounds was according to the following general method:

A solution of a 4-((1E,3E)-4-phenylamino-buta-1,3-dienyl)-chromenylium compound C (0.5 mmol) (Dyes and Pigments 17, 153(1991)) and 7-Dialkylamino-4-hydroxy-chromen-2-one B (0.5 mml) (J. Heterocycl. Chem 17, 225 (1980)) in 8 ml acetic acid anhydride/pyridine mixture was refluxed for eight hours. After cooling, diethylether was added and the ether solution was removed. The remaining precipitate was purified by column chromatography.

Synthesis of specific Type I coumarine/chinolone compounds was as follows; each of the cited references are expressly incorporated by reference herein:

V07-05146

Synthesis of 2-tert-butyl-7-diethylamino-4-[(1E,3E)-4-(7-diethylamino-4-hydroxy-2-oxo-2H-chromen-3-yl)-buta-1,3-dienyl]-chromenylium tetrafluoroborate (V07-05146) from 2-tert-Butyl-7-diethylamino-4-((1E,3E)-4-phenylamino-buta-1,3-dienyl)-chromenylium tetrafluoroborate and 7-diethylamino-4-hydroxy-chromen-2-one. Purification was on silica with toluene/ethanol gradient. Yield: 62 mg dark powder.

$C_{34}H_{41}N_2O_4^+BF_4^-$ (628.55 g/mol); MS (ES+) [m/z]: 541 [M$^+$]

$\lambda_{abs}$: 683 nm; $\lambda_{em}$: 715 nm; $\epsilon$: 90.000 mol$^{-1}$ cm$^-$ in MeOH

V07-05176

Synthesis of 7-[bis-(3-sulfo-propyl)-amino]-2-tert-butyl-4-[(1E,3E)-4-(7-dihexylamino-4-hydroxy-2-oxo-2H-chromen-3-yl)-buta-1,3-dienyl]-chromenylium sodium salt (V07-05176) from 2-tert-butyl-7-bis-(3-sulfo-propyl)-amino-4-((1E,3E)-4-phenylamino-buta-1,3-dienyl)-chromenylium tetrafluoroborate and 7-dihexylamino-4-hydroxy-chromen-2-one. Purification on PR-silica with methanol/water gradient. Yield: 30 mg dark powder $C_{44}H_{59}N_2O_{10}S_2^-Na^+$ (863.09 g/mol); MS (ES–) [m/z]: 419 [(M$^-$–H$^+$)$^{2-}$]; 839 [M$^-$]

$\lambda_{abs}$: 684 nm; $\lambda_{em}$: 723 nm; $\epsilon$: 140.000 mol$^{-1}$ cm$^-$ in MeOH

V07-05170

Synthesis of 7-[bis-(3-sulfo-propyl)-amino]-2-tert-butyl-4-[(1E,3E)-4-(7-diethylamino-4-hydroxy-2-oxo-2H-chromen-3-yl)-buta-1,3-dienyl]-chromenylium sodium salt (V07-05170) from 2-tert-butyl-7-bis-(3-sulfo-propyl)-amino-4-((1E,3E)-4-phenylamino-buta-1,3-dienyl)-chromenylium tetrafluoroborate and 7-Diethylamino-4-hydroxy-chromen-2-one Purification on PR-silica with methanol/water gradient. Yield: 25 mg dark powder $C_{36}H_{43}N_2O_{10}S_2^-Na^+$ (750.87 g/mol); MS (ES–) [m/z]: 363 [(M$^-$–H$^+$)$^{2-}$]; 727 [M$^-$]

$\lambda_{abs}$: 682 nm; $\lambda_{em}$: 717 nm; $\epsilon$: 90.000 mol$^{-1}$ cm$^{-1}$ in MeOH

V02-06006

Synthesis of 2-tert-butyl-4-[(1E,3E)-4-(7-diethylamino-4-hydroxy-2-oxo-2H-chromen-3-yl)-buta-1,3-dienyl]-7-[ethyl-(3-sulfo-propyl)-amino]-chromenylium betaine (V02-06006) from 2-tert-butyl-7-(3-sulfo-propyl)-ethyl-amino-4-((1E,3E)-4-phenylamino-buta-1,3-dienyl)-chromenylium tetrafluoroborate and 7-diethylamino-4-hydroxy-chromen-2-one. Purification was on PR-silica with methanol/water gradient. Yield: 45 mg dark powder $C_{35}H_{42}N_2O_7S$ (634.80 g/mol); MS (ES–) [m/z]: 633 [(M$^-$–H$^+$)$^-$];

$\lambda_{abs}$: 687 nm; $\lambda_{em}$: 712 nm; $\epsilon$: 75.000 mol$^{-1}$ cm$^-$ in MeOH Synthesis of another type II of coumarine/chinolone compounds was according to the following general method; each of the cited references are expressly incorporated by reference herein:

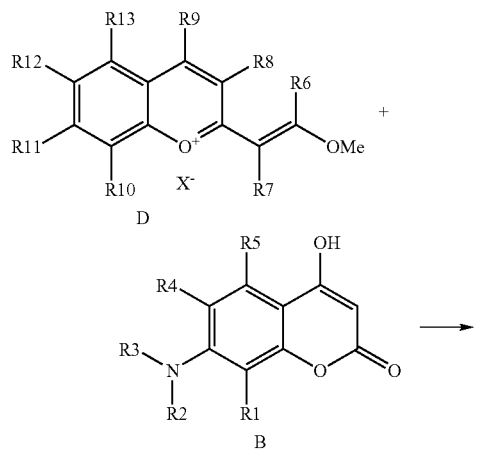

D

B

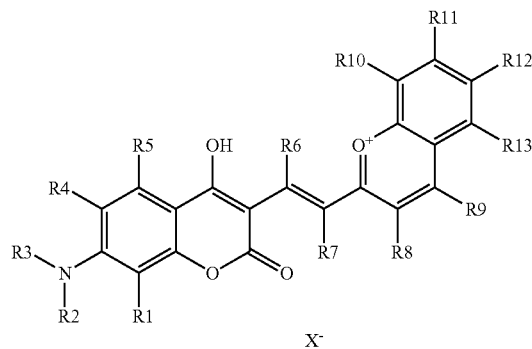

X$^-$

A solution of a 2-((E)-2-methoxy-vinyl)-chromenylium compound D (0.5 mmol) (J. Prakt. Chem 337, 216 (1995)) and 7-dialkylamino-4-hydroxy-chromen-2-one B (0.5 mml) (J. Heterocycl. Chem. 17, 225 (1980)) in 8 ml acetic acid anhydride/pyridine mixture was refluxed for four hours. After cooling, diethylether was added and the ether solution was removed. The remaining precipitate was purified by column chromatography.

Synthesis of specific Type II coumarine/chinolone compounds was as follows:

V07-05143

Synthesis of 4-tert-butyl-7-diethylamino-2-[(E)-2-(7-diethylamino-4-hydroxy-2-oxo-2H-chromen-3-yl)-vinyl]-chromenylium tetrafluoroborate (V07-05143) was from 2-((E)-2-methoxy-vinyl)-7-diethylamino-4-tert-butyl-chromenylium tetrafluoroborate and 7-diethylamino-4-hydroxy-chromen-2-one. Purification was on silica with toluene/ethanol gradient. Yield: 90 mg dark powder $C_{32}H_{39}N_2O_4^+BF_4^-$ (602.48 g/mol); MS (ES+) [m/z]: 515 [M$^+$]

$\lambda_{abs}$: 636 nm; $\lambda_{em}$: 666 nm; $\epsilon$: 95.000 mol$^{-1}$ cm$^-$ in MeOH

V07-03034

Synthesis of 6-diethylamino-4-[1-(7-diethylamino-4-hydroxy-2-oxo-2H-chromen-3-yl)-meth-(E)-ylidene]-1,2,3,4-tetrahydro-xanthenylium perchlorate from 6-diethylamino-4-[1-methoxy-meth-(E)-ylidene]-1,2,3,4-tetrahydro-xanthenylium perchlorate and 7-diethylamino-4-hydroxy-chromen-2-one. Purification was on silica with toluene/ethanol gradient. Yield: 80 mg dark powder $C_{31}H_{35}N_2O_4^+ClO_4^-$ (599.09 g/mol); MS (ES+) [m/z]: 499 [M$^+$]

$\lambda_{abs}$: 680 nm; $\lambda_{em}$: 7070 nm; E: 110.000 mol$^{-1}$ cm$^-$ in MeOH In another embodiment, compounds referred to herein as Martina dyes are disclosed. They have absorbance maxima, depending on specific substituents, from about 500 nm to about 800 nm, and have emission maxima from about 530 nm to about 830 nm. Martina dyes have the following general formulas I-V as, as described.

In one embodiment, Martina type dyes of general Martina formula I

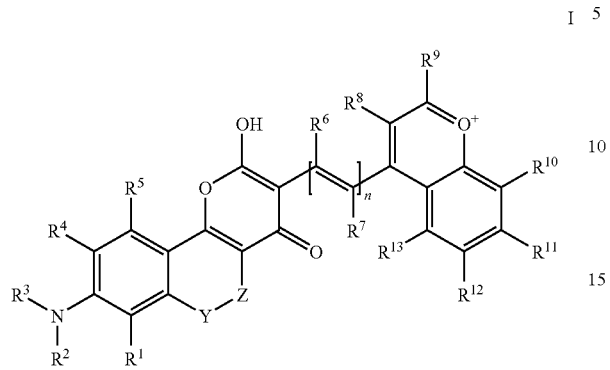

and general Martina formula II

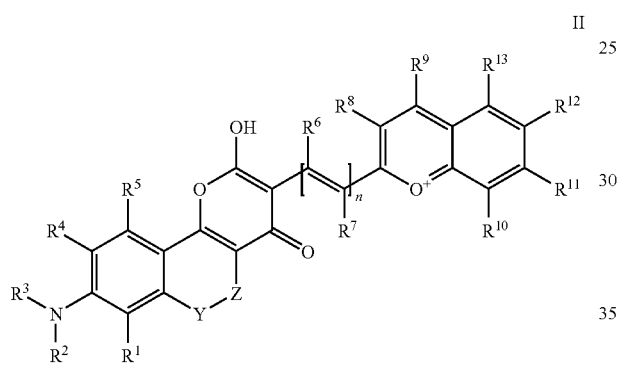

are disclosed. In Martina dyes of each of general formulas I and II, $R^1$ to $R^{10}$, $R^{12}$, and $R^{13}$ are the same or different and are selected from the group consisting of hydrogen, chlorine, bromine, sulfonate, alkyl, ter.-alkyl, aryl, carboxyaryl, heteroaryl, cycloalkyl, heterocycloalkyl, cyano, hydroxy, alkyloxy, alkylmercapto, aryloxy, arylmercapto, heteroaryloxy, heteroarylmercapto, hydroxyalkyl, carboxyalkyl, sulfoalkyl and cyanoalkyl-residues, or are N-mono- or N.N-di-alkylsubstituted amino or cyclic amino functions, $R^{11}$ is $OR^{14}$ or $NR^{15}R^{16}$ whereby $R^{14}$-$R^{16}$ can have the same or different functionalities equal to $R^1$-$R^{10}$, $R^1$ and $R^2$, and/or $R^2$ and $R^3$, and/or $R^3$ and $R^4$, and/or $R^7$ and $R^8$, and/or $R^{10}$ and $R^{14}$, and/or $R^{12}$ and $R^{14}$, and/or $R^{10}$ and $R^{15}$, and/or $R^{12}$ and $R^{16}$, and/or $R^{15}$ and $R^{16}$, can form further substituted aliphatic or aromatic ring systems, $R^6$ and $R^7$ are the same or different, whereby aliphatic bridges between neighboring or in 1,3-position to each other located $R^6$— or $R^7$-substituents are possible if n=2, 3, or 4, Y-Z is selected from the group consisting of O, S, $NR^{17}$, $CR^{18}R^{19}$, O—CO, CO—O, $NR^{17}$—CO, $CR^{18}R^{19}$—O, O—$CR^{18}R^{19}$, and $CR^{18}R^{19}$—$CR^{20}R^{21}$, whereby $R^{17}$-$R^{21}$ can have the same or different functionalities equal to $R^1$-$R^{10}$, and n=0 to 4.

In another embodiment, Martina dyes of the general Martina formula III

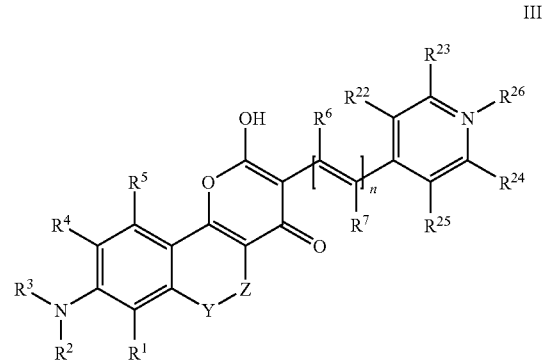

and Martina dyes of the general Martina formula IV

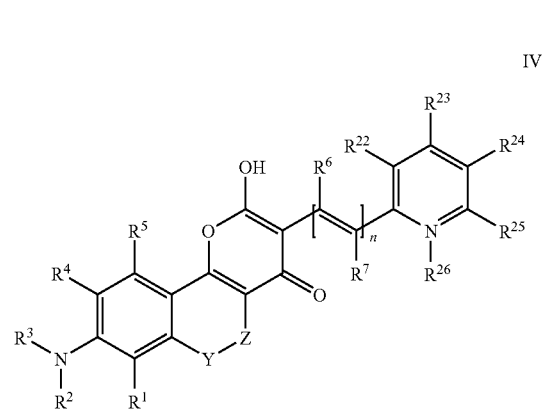

are disclosed. In Martina dyes of each of general formulas III and IV, $R^1$ to $R^7$ and $R^{22}$-$R^{26}$ are the same or different and are selected from the group consisting of hydrogen, chlorine, bromine, sulfonate, alkyl, ter.-alkyl, aryl, carboxyaryl, heteroaryl, cycloalkyl, heterocycloalkyl, cyano, hydroxy, alkyloxy, alkylmercapto, aryloxy, arylmercapto, heteroaryloxy, heteroarylmercapto, hydroxyalkyl, carboxyalkyl, sulfoalkyl and cyanoalkyl-residues, or are N-mono- or N.N-di-alkylsubstituted amino or cyclic amino functions, $R^1$ and $R^2$, and/or $R^2$ and $R^3$, and/or $R^3$ and $R^4$, and/or $R^7$ and $R^{22}$, and/or $R^{22}$ and $R^{23}$, and/or $R^{24}$ and $R^{25}$ can form further substituted aliphatic or aromatic ring systems, $R^6$ and $R^7$ are the same or different or different, whereby aliphatic bridges between neighboring or in 1,3-position to each other located $R^6$— or $R^7$-substituents are possible if n=2, 3, or 4, Y-Z is selected from the group consisting of O, S, $NR^{17}$, $CR^{18}R^{19}$, O—CO, CO—O, $NR^{17}$—CO, $CR^{18}R^{19}$—O, O—$CR^{18}R^{19}$, and $CR^{18}R^{19}$—$CR^{20}R^{21}$, whereby $R^{17}$-$R^{21}$ can have the same or different functionalities equal to $R^1$-$R^7$, and n=0 to 4.

In another embodiment, Martina dyes of the general Martina formula V

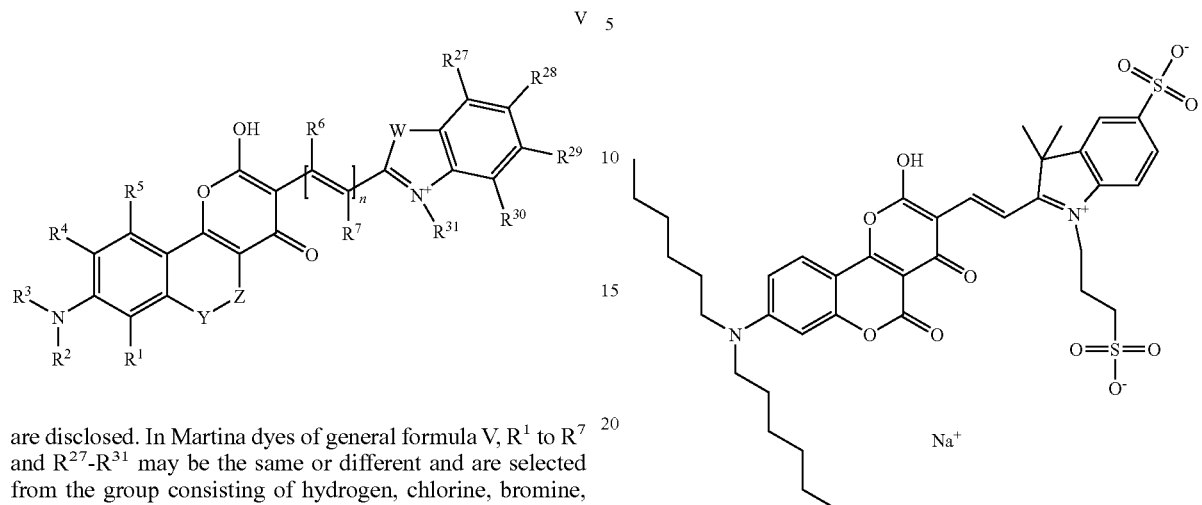

are disclosed. In Martina dyes of general formula V, $R^1$ to $R^7$ and $R^{27}$-$R^{31}$ may be the same or different and are selected from the group consisting of hydrogen, chlorine, bromine, sulfonate, alkyl, ter.-alkyl, aryl, carboxyaryl, heteroaryl, cycloalkyl, heterocycloalkyl, cyano, hydroxy, alkyloxy, alkylmercapto, aryloxy, arylmercapto, heteroaryloxy, heteroarylmercapto, hydroxyalkyl, carboxyalkyl, sulfoalkyl and cyanoalkyl-residues, or are N-mono- or N.N-di-alkylsubstituted amino or cyclic amino functions, $R^1$ and $R^2$, and/or $R^2$ and $R^3$, and/or $R^3$ and $R^4$, and/or $R^{27}$ and $R^{28}$, and/or $R^{28}$ and $R^{29}$ and/or $R^{29}$ and $R^{30}$ can form further substituted aliphatic or aromatic ring systems, $R^6$ and $R^7$ are the same or different, whereby aliphatic bridges between neighboring or in 1,3-position to each other located $R^6$— or $R^7$-substituents are possible if n=2, 3, or 4, Y-Z is selected from the group consisting of O, S, $NR^{17}$, $CR^{18}R^{19}$, O—CO, CO—O, $NR^{17}$—CO, $CR^{18}R^{19}$—O, O—$CR^{18}R^{19}$, and $CR^{18}R^{19}$—$CR^{20}R^{21}$, whereby $R^{17}$-$R^{12}$ can have the same or different functionalities equal to $R^1$-$R^7$, W is selected from the group consisting of O, S, $NR^{32}$, and $CR^{33}R^{34}$, whereby $R^{32}$-$R^{34}$ can have the same or different functionalities equal to $R^1$-$R^7$, and n=0 to 4.

One embodiment of Martina type dyes of general formula I is the structure designated as V07-06050 "Martina Red", as follows:

V07-06050 "Martina Red"

Another embodiment of Martina type dyes of general formula V are the following structures designated as V07-05167 "Martina Orange", V07-03189, and V02-06086, as follows:

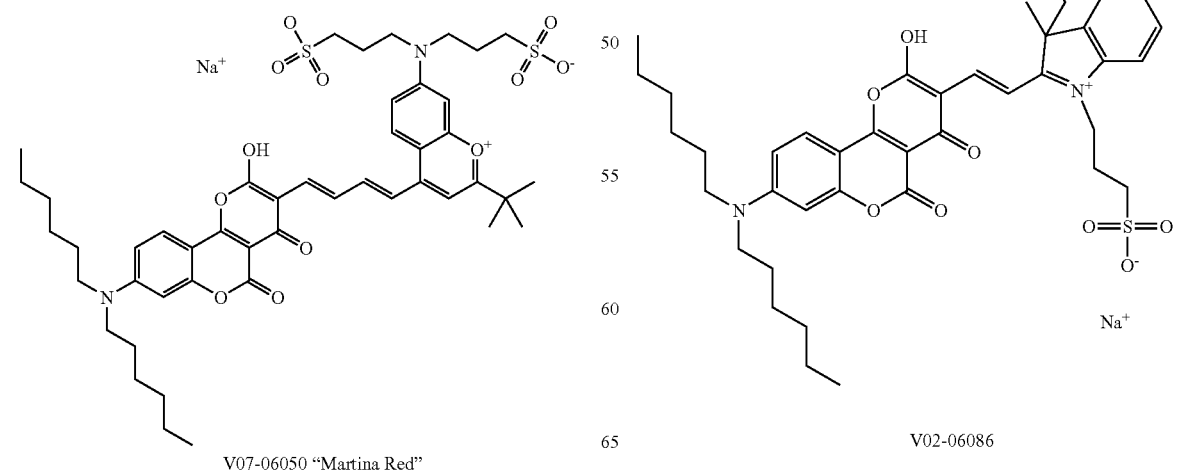

V07-05167 "Martina Orange"

V07-03189

V02-06086

Selected characteristics of the Martina dyes are presented in Table 2.

TABLE 2

| | MW g/mol | Molar Absorbance ε mol$^{-1}$cm$^{-1}$ in MeOH | Absorption Max. $\lambda_{abs}$ nm | Emission Max. $\lambda_{em}$ nm |
|---|---|---|---|---|
| V07-05167 (Martina Orange) | 806.93 | 125,000 | 520 in MeOH 523 with BSA | 563 nm in PBS 542 with BSA |
| V07-06050 (Martina Red) | 931.12 | 81,000 | 684 in MeOH | 716 nm in MeOH |
| V07-03189 | 776.95 | 88,000 | 520 in MeOH | 562 in MeOH |
| V02-06086 | 879.00 | 91,000 | 522 in MeOH | 560 in MeOH |

When V07-05167 (Martina Orange) was formulated as a dye, it stained a broad range of proteins (e.g., acidic, basic, etc.). When used to stain proteins separated on a gel (e.g., by polyacrylamide gel electrophoresis (PAGE)), protein detection sensitivity was 0.5 ng/band in one embodiment, and was 0.1 ng/band in another embodiment.

When V07-06050 (Martina Red) was formulated as a dye, protein detection sensitivity was less than 0.5 ng.

Martina dyes of any of general formulas I, II, III, IV, and/or V, previously described, are disclosed as compounds, compositions, and method for using the compositions. In one embodiment, compositions of Martina dyes are used as biocompatible protein stains, either in vivo (e.g., cultured cells, tissue cultures, etc.) or in vitro.

Synthesis of one type of Martina-type compounds (Type I), those of the type to which the specific Martina Red compound belongs, was according to the following general method; each of the cited references are expressly incorporated by reference herein:

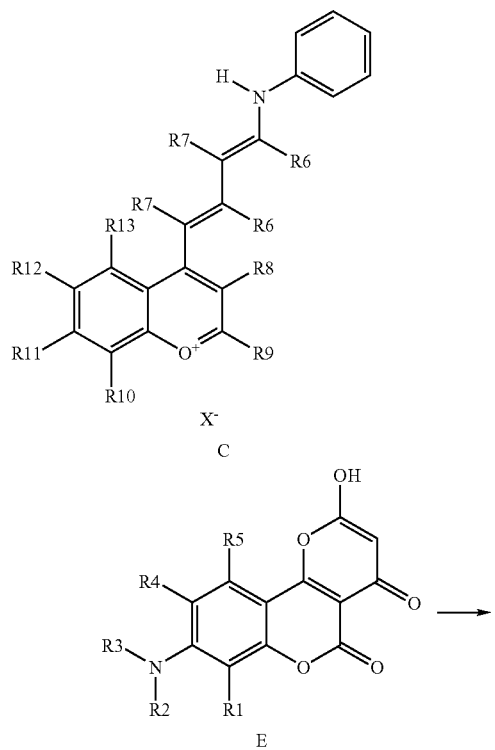

C

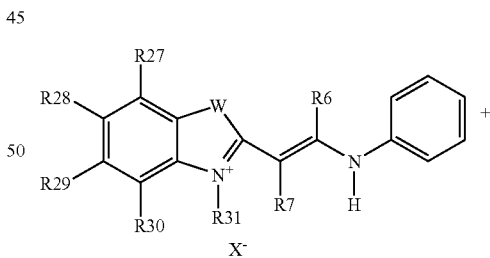

E

-continued

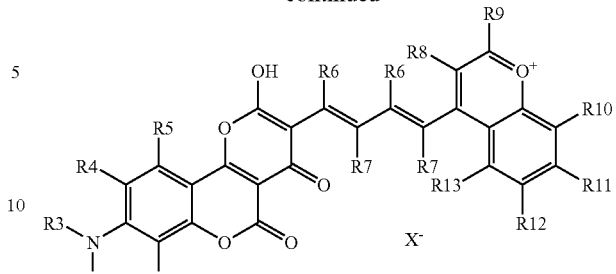

A solution of a 4-((1E,3E)-4-phenylamino-buta-1,3-dienyl)-chromenylium compound C (0.5 mmol) (Dyes and Pigments 17, 153 (1991)) and 8-dialkylamino-2-hydroxy-pyrano[3,2-c]chromene-4,5-dione E (0.5 mml) (Monatsh. Chem. 111, 93 (1980)) in 10 ml acetic acid anhydride/pyridine mixture was refluxed for eight hours. After cooling, diethylether was added and the ether solution was removed. The remaining precipitate was purified by column-chromatography.

Synthesis of the specific Martina Red compound was as follows; each of the cited references are expressly incorporated by reference herein:

V07-06050 (Martina Red)

Synthesis of 7-[bis-(3-sulfo-propyl)-amino]-2-tert-butyl-4-[(1E,3E)-4-(8-dihexylamino-2-hydroxy-4,5-dioxo-4H,5H-pyrano[3,2-c]chromen-3-yl)-buta-1,3-dienyl]-chromenylium sodium salt from 2-tert-butyl-7-[bis-(3-sulfo-propyl)-amino]-4-((1E,3E)-4-phenylamino-buta-1,3-dienyl)-chromenylium sodium salt and 8-dihexylamino-2-hydroxy-pyrano[3,2-c]chromen-4,5-dione. Purification was on RP-silica with methanol/water gradient. Yield: 102 mg dark powder $C_{47}H_{59}N_2O_{12}S_2^-Na^+$ (931.12 g/mol); MS (ES−) [m/z]: 453 [(M$^-$−H$^+$)$^{2-}$]; 929 [(M$^-$−H$^+$+Na$^+$)]

$\lambda_{abs}$: 684 nm; $\lambda_{em}$: 717 nm; ε: 81.000 mol$^{-1}$ cm$^{-1}$ in MeOH Synthesis of another type of Martina-type compounds (Type V), those of the type to which the specific Martina Orange compound belongs, was according to the following general method

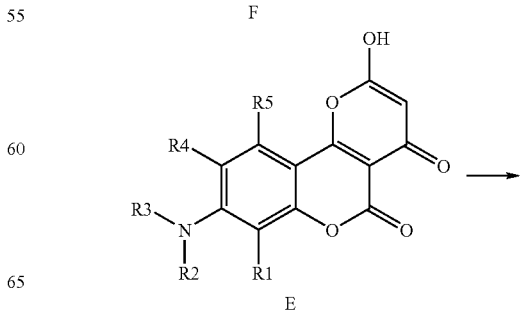

F

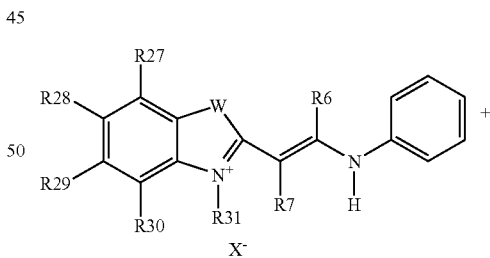

E

-continued

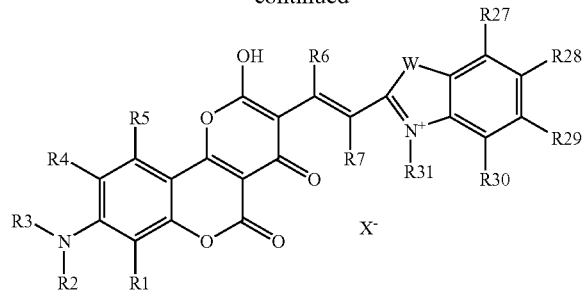

A solution of a substituted 2-((E)-2-phenylamino-vinyl)-3H-indolium compound F (0.5 mmol)(Bioconjugate Chem. 4, 105 (1993)) and the 8-dialkylamino-2-hydroxy-pyrano[3,2-c]chromene-4,5-dione E (0.5 mmol) (Monatsh. Chem. 111, 93 (1980)) in 10 ml acetic acid anhydride/pyridine mixture was refluxed for eight hours. After cooling, diethylether was added and the ether solution was removed. The remaining precipitate was purified by column-chromatography.

Synthesis of Martina Orange type compounds and Martina Orange compound was as follows:

V07-05167 (Martina Orange)

Synthesis of 2-[(E)-2-(8-Dihexylamino-2-hydroxy-4,5-dioxo-4H,5H-pyrano[3,2-c]chromen-3-yl)-vinyl]-3,3-dimethyl-5-sulfo-1-(3-sulfo-propyl)-3H-indolium sodium salt (V07-05167 Martina Orange) from 1-(3-sulfo-propyl)-3,3-dimethyl-2-((E)-2-phenylamino-vinyl)-5-sulfo-3H-indolium sodium salt and 8-Dihexylamino-2-hydroxy-pyrano[3,2-c]chromen-4,5-dione. Purification was on RP-silica with methanol/water gradient. Yield: 190 mg red powder $C_{39}H_{47}N_2O_{11}S_2$-Na$^+$ (806.93 g/mol); MS (ES−) [m/z]: 391 [(M$^-$−H$^+$)$^{2-}$]; 783 [M$^-$]; 805 [(M$^-$−H$^+$+Na$^+$)]

$\lambda_{abs}$: 520 nm; $\lambda_{em}$: 563 nm; $\epsilon$: 125.000 mol$^{-1}$ cm$^{-1}$ in MeOH

V07-03189

Synthesis of 1-(5-carboxy-pentyl)-2-[(E)-2-(8-dihexylamino-2-hydroxy-4,5-dioxo-4H,5H-pyrano[3,2-c]chromen-3-yl)-vinyl]-3,3-dimethyl-5-sulfo-3H-indolium betaine (V07-03189) from 1-(5-carboxy-pentyl)-3,3-dimethyl-2-((E)-2-phenylamino-vinyl)-5-sulfo-3H-indolium betaine and 8-Dihexylamino-2-hydroxy-pyrano[3,2-c]chromen-4,5-dione Purification on RP-silica with methanol/water gradient. Yield: 122 mg red powder $C_{42}H_{52}N_2O_{10}S$ (776.95 g/mol); MS (ES−) [m/z]: 775 [(M−H$^+$)$^-$]

$\lambda_{abs}$: 520 nm; $\lambda_{em}$: 562 nm; $\epsilon$: 88.000 mol$^{-1}$ cm$^{-1}$ in MeOH

V02-06086

Synthesis of 3-(3-carboxy-propyl)-2-[(E)-2-(8-dihexylamino-2-hydroxy-4,5-dioxo-4H,5H-pyrano[3,2-c]chromen-3-yl)-vinyl]-3-methyl-5-sulfo-1-(3-sulfo-propyl)-3H-indolium sodium salt (V02-06086) from 1-(3-sulfo-propyl)-3-methyl-3-(3-carboxy-propyl)-2-((E)-2-phenylamino-vinyl)-5-sulfo-3H-indolium sodium salt and 8-Dihexylamino-2-hydroxy-pyrano[3,2-c]chromen-4,5-dione. Purification was on RP-silica with methanol/water gradient. Yield: 110 mg red powder $C_{42}H_{51}N_2O_{13}S_2$-Na$^+$ (879.00 g/mol); MS (ES−) [m/z]: 427 [(M$^-$−H$^+$)$^{2-}$]; 877 [(M$^-$−H$^+$+Na$^+$)]

$\lambda_{abs}$: 522 nm; $\lambda_{em}$: 560 nm; $\epsilon$: 88.000 mol$^{-1}$ cm$^-$ in MeOH.

To form a composition (dye), at least one biocompatible excipient is added to the compound(s). The compounds were compatible with a broad range of buffers over the pH range of about pH 4 to about pH 11. The following buffers can be used to enhance detection sensitivity (level of protein detection) and include, but are not limited to, short chain organic acids (R—$CO_2$) where R=H, —$CH_3$, —$CH_2$—$CH_3$, —$CH_2$—$CH_2$—$CH_3$, —$CH_2$—$CH_2$—$CH_2$—$CH_3$, etc, inorganic buffers such as phosphate and borate salts, and/or organic buffers such as TRIS (tris[hydroxymethyl]aminomethane hydrochloride), CAPS (3-[cyclohexylamino]-1-propanesulfonic acid), CHES (2-[cyclohexylamino)ethanesulfonic acid), MES (2-[N-morpholino]ethanesulfonic acid), HEPES (N-[2-hydroxyethyl]piperazine-N'-[2-ethanesulfonic acid]), and MOPS (3-[N-morpholino]propanesulfonic acid). The buffer concentration ranged from about 10 mM to about 1 M. In one embodiment, the pH ranged from about pH 3 to about pH 5. In another embodiment, the pH ranged from about pH 8 to about pH 10. In one embodiment, the buffer pH was adjusted using either sodium or potassium hydroxide.

Additives that assist in solubilizing and stabilizing the compound in solution may be included. Examples of such additives that assist in solubilization, stabilization, photostability, etc. include, but are not limited to, an alcohol (R—OH) at about 0.1% v/v to about 20% v/v such as methanol, ethanol or isopropanol; and/or a diol at about 1% v/v to about 20% v/v such as 1,2-propanediol, propane-1,3-diol, butane-1,2-diol, butane-1,3-diol, butane-1,4-diol, butane-2,3-diol, pentane-1,2-diol, pentane-1,3-diol, pentane-1,4-diol, pentane-1,5-diol, pentane-2,3-diol, pentane-2,4-diol, hexane-2,3-diol, and/or hexane-2,5-diol.

In one embodiment, the composition may also contain benzaldehyde. For example, benzaldehyde at a concentration of at least 50 mM increased the absorbance and fluorescent intensity, dye stability, dye photostability, and detection sensitivity of the dyes.

In one embodiment, the composition may also contain polyethylene glycol (PEG) and/or polyvinyl alcohol (PVA) at about 0.1% v/v to about 5% v/v. Embodiments containing the disclosed compound(s) and PEG and/or PVA have reduced background, and thus provide enhanced sensitivity by increasing the signal to noise ratio.

In one embodiment, dyes that have high extinction coefficients and, upon binding to proteins, display an increase in fluorescence intensity or result in a wavelength change, may be further modified with chelating reagents for non-specific protein binding. Chelating reagents include iminodiacetic acid (IDA), nitrilotriacetic acid (NTA), 1,2 bis(o-aminophenoxy)ethane N,N,N'N' tetraacetic acid (BAPTA), and diimines. Metals used for chelating to the dyes and binding to proteins can include nickel and copper. Such modified dyes may be used in non-specific protein assays and as non-specific protein stains. If the dyes retain their fluorescent properties after being modified, the metal chelation may result in an increased binding between the protein and the dye. This type of binding via the metal may also provide detergent compatibility to protein assays. Such compatibility is needed to assay protein samples that contain detergents because fluorescent dyes bind to detergents in addition to binding to proteins, which may lead to falsely elevated protein assay results. In one embodiment, multiple chelating groups may be added to increase binding and detergent compatibility in protein assays. The metal chelating modification could be made in addition to other modifications with groups such as sulfonates and alkyl chains that increase binding between the dye and protein. In another embodiment, total detergent compatibility may be obtained by modifying dyes so that they bind to proteins only via the chelated metal, for example, by removing hydrophobic groups and adding hydrophilic groups. This embodiment eliminates direct binding of the dye to either the protein or the detergent.

In another embodiment, dyes that have high extinction coefficients and, upon binding to proteins, display an increase in fluorescence intensity or result in a wavelength change, may further be modified with chelating reagents for group-specific staining, such as for histidine-tagged proteins or for phosphoproteins. Such dyes, modified such that the fluorescent properties of the dyes are not altered, with added hydrophilic groups and free of hydrophobic groups (to reduce non-specific binding between the dye and the protein) may be further modified with a metal chelating group and a metal, such as gallium, iron, cobalt, or nickel. The metal chelated dye may be used to detect tagged proteins in solution or on a solid support (e.g., gel, membrane, etc.).

In one embodiment, dyes such as Martina Orange and/or Martina Red may be modified with hydrophilic groups (e.g. sulfonates, carboxylic acids, polyethylene glycol (PEG) chains, etc.). This could result in enhanced fluorescence when specific binding occurs between the metal that is chelated to the dye (e.g. gallium for phosphoproteins) and the specific group of proteins. Such modification differs from metal-chelated dyes, such as DY649 (Dyomics, Jena Germany) that do not exhibit a change in fluorescence upon binding to proteins, and hence results in poor signal to noise ratios.

In one embodiment, a dye having high extinction coefficients and, upon binding to proteins, displays an increase in fluorescence intensity or results in a wavelength change, and modified with hydrophilic groups and lacking hydrophobic groups that do not alter the fluorescence properties of the dyes, may be further modified with reactive groups. Such reactive groups include iodoacetyl, maleimide, hydrazides, N-hydroxysuccinimides, sulfonyl chloride, phenylazides, etc. Specific reactive groups on the dye react with and detect specific groups, such as primary amines, sulfydryls or sugars. Enhanced fluorescence intensity or wavelength change is obtained when the desired reaction occurs.

Dyes modified with such reactive groups may be used to label macromolcules (e.g., antibodies, streptavidin, etc) using methods known to one skilled in the art. For example, Streptavidin, reconstituted or dialyzed against sodium borate or sodium carbonate buffer, between pH 8.5 to pH 9.0, may be reacted with a 5-10 molar excess of N-hydroxysuccnimide activated Martina Orange that is sulfonated and free of hydrophobic groups. The reaction is carried out for one to two hours at room temperature (about 20° C. to about 22° C.) and then dialyzed against several changes of phosphate buffered saline (pH 7.2). The resulting dye-macromolecule conjugates may be used in applications such as in detection of specific proteins in immunoassays, sugars in glycoproteins with lectins, protein-protein interactions, oligonuceleotides in nucleic acid, hybridization, and in Electrophoretic Mobility Shift Assays (EMSA).

In one embodiment, a dye that fluoresces at one set of excitation and emission wavelengths can be used with at least one other dye that fluoresces at another set of excitation and emission wavelengths in a multiplexing assay. One detection assay using one fluorescent dye for detecting one type of group, e.g., phosphoproteins, and in another assay using another dye fluorescing at another set of wavelengths, may be used to detect total protein in the same sample. Both detections can be performed simultaneously in a multiplexing assay. The specific dye and detections (e.g., phosophoproteins, glycoprotein, immunodectection, protein-protein interactions, DNA-protein assays, total proteins, in-cell applications, fluorescence resonance energy transfer (FRET), flow cytometry, etc. may be determined by routine experimentation as known by one skilled in the art.

In another embodiment a combination of these dyes can be used to design a dye with desired spectral characteristics by sandwiching a chromophore between two fluorophores. These dyes can be used as donors or acceptors or both for the FRET (fluorescence resonance energy transfer) based assays. For FRET assays a highly emissive donor and an acceptor are required. The best donor-acceptor pair can be determined by the overlap of emission spectra of donor and absorbance spectra of acceptor. The efficiency of the FRET assay depends on the overlap between the emission of the donor dye and excitation of the acceptor dye.

In one embodiment these dyes can be chelated with, for example, BAPTA for chelating calcium, crown ethers for chelating sodium or potassium, etc. and used as fluorescence intensity based sensors for cations or anions. The metal chelated dyes change spectral properties after binding with analytes of interests, such as $Ca^{+2}$, $K^+$, $Na^+$, $Zn^+$, $Cl^-$. Such structures are shown below:

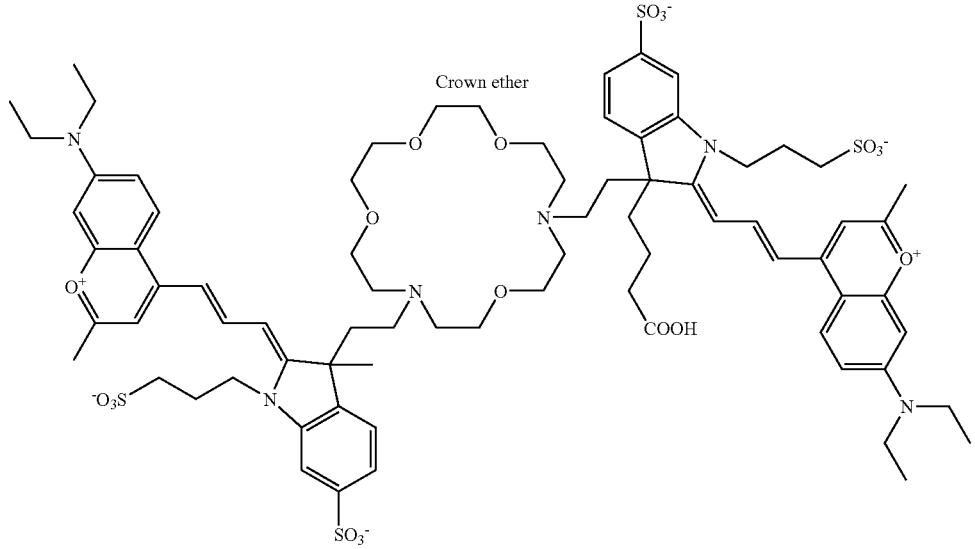

Sensor Dye1

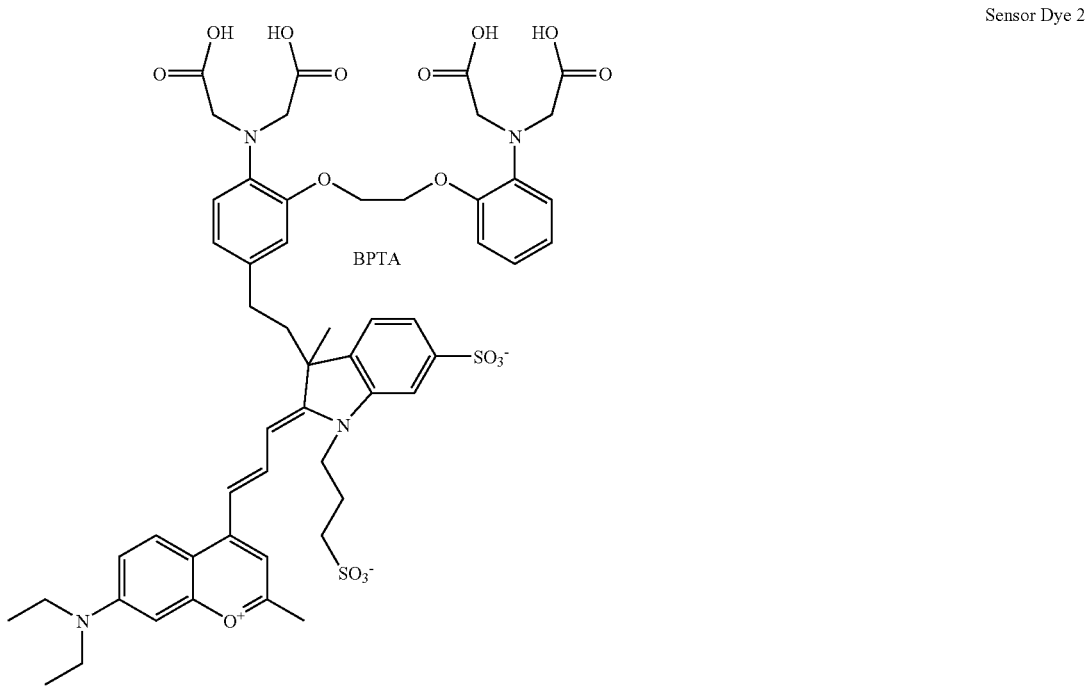

Sensor Dye 2

In one embodiment, these compounds can be use as an indicator to monitor pH by attaching specific sensitive moieties to one end of the dye, as shown in the following structure:

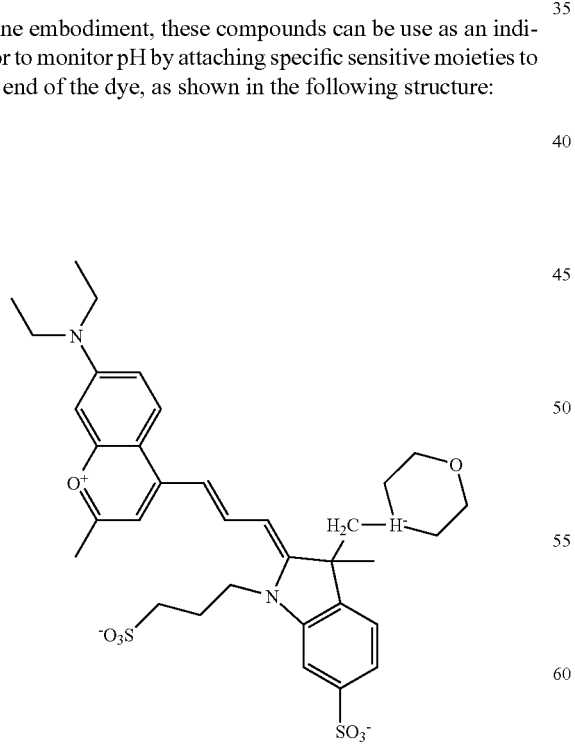

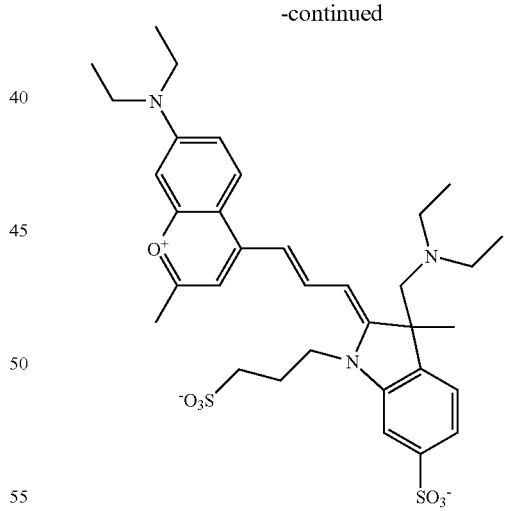

Possible pH indicator Dyes

The method encompasses any qualitative and/or quantitative determination of the presence, characterization, function, etc. of one or more peptides and/or proteins. One or more coumarine/chinolone and/or Martina-type dyes bind to proteins in solution or proteins that have been separated from a mixture. Proteins may be separated by polyacrylamide gel electrophoresis followed by a wash/fix procedure and detected and/or assayed in the gel. Alternatively, separated proteins may be transferred to a membrane and detected and/or separated in the membrane. These dyes may also be used to quantitate proteins in solution.

A solution of the coumarine/chinolone and/or Martina-type dye(s) is applied to separated proteins or added to a protein solution and incubated for a time sufficient to stain the proteins. In one embodiment, incubation may be for about one hour. After incubation, the coumarine/chinolone and/or Martina-type dye(s) bound to proteins are detected directly or indirectly, and by any method (e.g., visually, by qualitative and/or quantitative scanning using a fluorescent imaging system, etc.). In embodiments where proteins are separated, the gel or membrane is washed with water or a dilute alcohol/acid mixture before dye incubation.

Modifications to the coumarine/chinolone and/or Martina-type compounds are encompassed by the method, as appreciated by one skilled in the art. For example, to enhance hydrophilicity, the chromophore/dye can be substituted with sulfonate, alkylsulfonate, hydroxy, (poly)hydroxyalkyl, carboxy, (poly)carboxyalkyl, and/or PEG substituents. To enhance the lipophilic character, the chromophore/dye can be substituted with aliphatic substituents. To shift and fine tune the absorption/emission wavelength of the chromophores/dyes, the number of vinylene units between the two terminal heterocycles can be varied, or additional (alkyl)amino, hydroxy-, and/or alkoxy substituents can be added on an electron-deficient position of the chromophore/dye. In embodiments where the dyes are substituted with a carboxy (alkyl) substituent, this functionality can be used to couple the chromophore/dye via an acid amide function to a biomolecule and/or to a ligand or ligand system.

The method and compositions will be further appreciated with respect to the following non-limiting examples.

Example 1

Solutions of the following concentrations were used to determine fluorescence of protein-dye solutions with varying protein-dye ratios. For the dye, a solution of any of the Red/Near IR dyes in PBS (22 mM, pH 7.2) with a concentration of $2*10^{-6}$ mol/l, is prepared. For the protein, five different solutions of bovine serum albumin (BSA) in PBS (see above) were prepared at the following concentrations: $2\times10^{-6}$ mol/l; $1\times10^{-5}$ mol/l; $2\times10^{-5}$ mol/l; $1\times10^{-4}$ mol/l; and $2\times10^{-4}$ mol/l. The dye solution (1.5 ml) and the corresponding protein solution (1.5 ml) were mixed for determining fluorescence. The highest protein concentration was assayed first, then a protein/dye ratio of 100:1 was adjusted. The value of the fluorescence was set as maximum and the subsequent values were related to it.

As shown in FIG. 1, none of the dye solutions will show any appreciable fluorescence in the absence of protein. In the presence of protein (e.g., BSA) an increase of the fluorescence will be observed. Expected fluorescence of solutions having different protein:dye ratios. The protein may be bovine serum albumin (BSA). The dye may be any of the disclosed red/near IR dyes.

Example 2

The procedure of Example 1 is followed except that any of the disclosed Martina-type dyes are substituted for the Red/Near IR dyes. The results are expected to be substantially the same.

Example 3

The coumarine/chinolone and/or Martina-type dyes were used to stain proteins and/or polymers of single amino acids (e.g., poly-alanine, poly-histidine, poly-lysine, etc.). Selected polymers of single amino acids (200 ng/spot) and proteins (500 ng/spot, 50 ng/spot, 5 ng/spot, and 0.5 ng/spot) were spotted onto nitrocellulose membranes (for amino acids: ALA alanine; ARG arginine; ASN asparagine; ASP aspartic acid; HIS histidine; LYS lysine; TYR tyrosine; TRP tryptophan, for proteins BSA bovine serum albumin; HRP horseradish peroxidase; Lys lysozyme).

The membranes were stained with the coumarine/chinolone and/or Martina-type dyes dissolved in water at 100 ng/ml. Membranes were stained for fifteen minutes and then washed in water for five minutes. The membranes were imaged at 680 nm excitation and 720 nm emission using an Odyssey Infrared Imaging System (LI-COR Biosciences).

Figure 2:
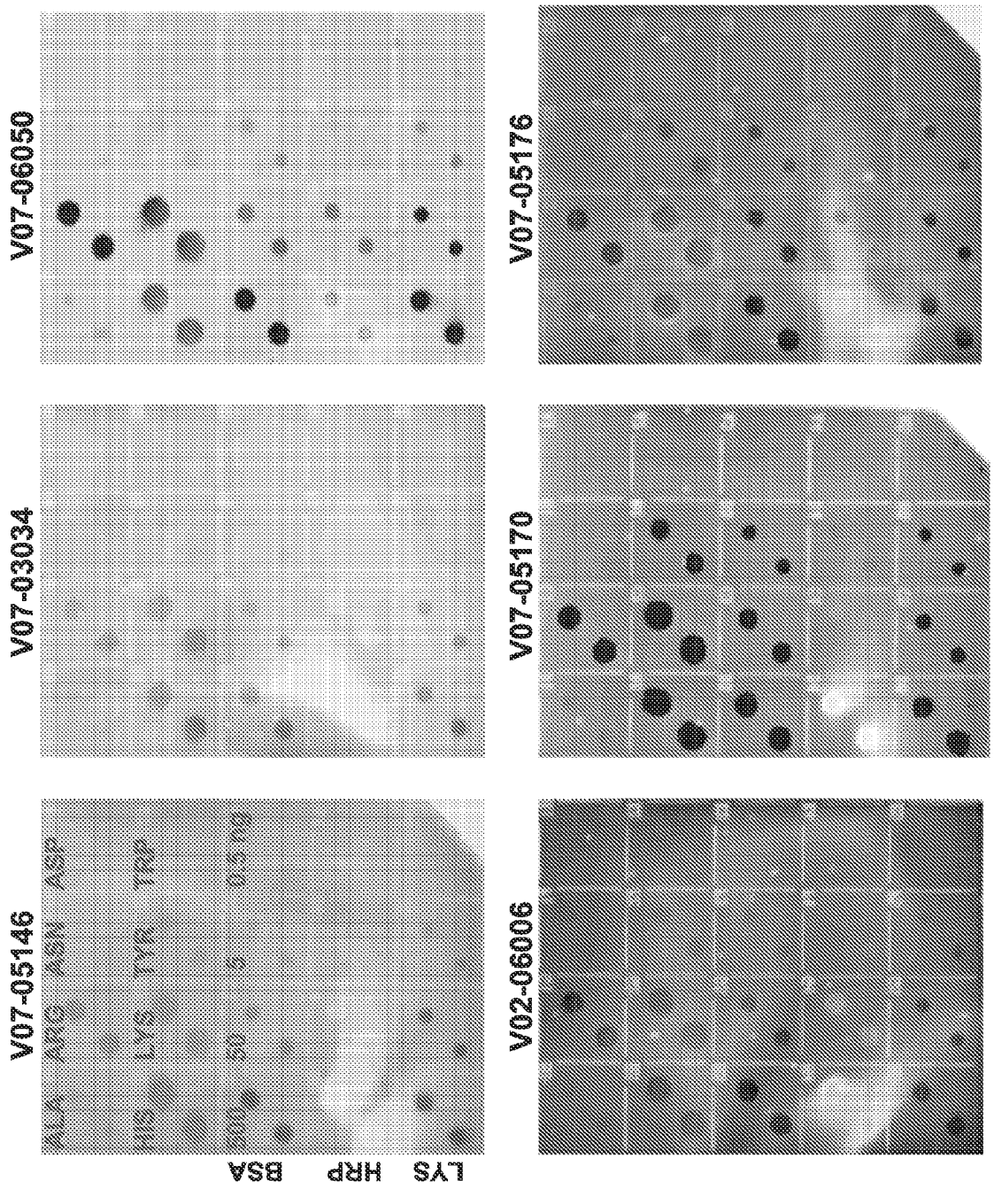
FIG. 2 shows use of coumarine/chinolone and/or Martina-type dyes to stain amino acids and proteins spotted on membranes.

Results are shown in FIG. 2. V07-03034, V07-05170, V07-05146 and V02-06006 had high background levels. Of the six compounds tested, V07-06050 and V07-05176 had the lowest background. The fluorescent intensity was higher with V07-06050, V07-05170 and V02-06006. The V07-06050 dye had the overall best fluorescent signal with the lowest background.

Example 4

Proteins were separated on a gel following electrophoresis and stained with the disclosed coumarine/chinolone and/or Martina-type dyes. A protein standard containing myosin, β-galactosidase, phosphorylase B, bovine serum albumin, ovalbumin, carbonic anhydrase, soybean trypsin inhibitor, lysozyme, and aprotinin was serially diluted from 1,000 ng to 0.12 ng per protein band. The proteins in the standard were separated by electrophoresis in 4-20% Tris-Glycine gel (Invitrogen) and stained with coumarine/chinolone and/or Martina-type dyes diluted in water at 100 ng/ml. The gels were washed following staining using a five minute 5% (v/v) acetic acid wash and two, ten minute water washes. Gels were imaged on a Typhoon 9410 Variable Mode Imager (GE Healthcare) using 532 nm laser, 580 BP 30 emission filter (Martina Orange) or an Odyssey Infrared Imaging System (LI-COR Biosciences) using 680 nm laser, 720 nm emission (V07-06050, V02-06006, V02-05170, and V07-05176).

Figure 3:
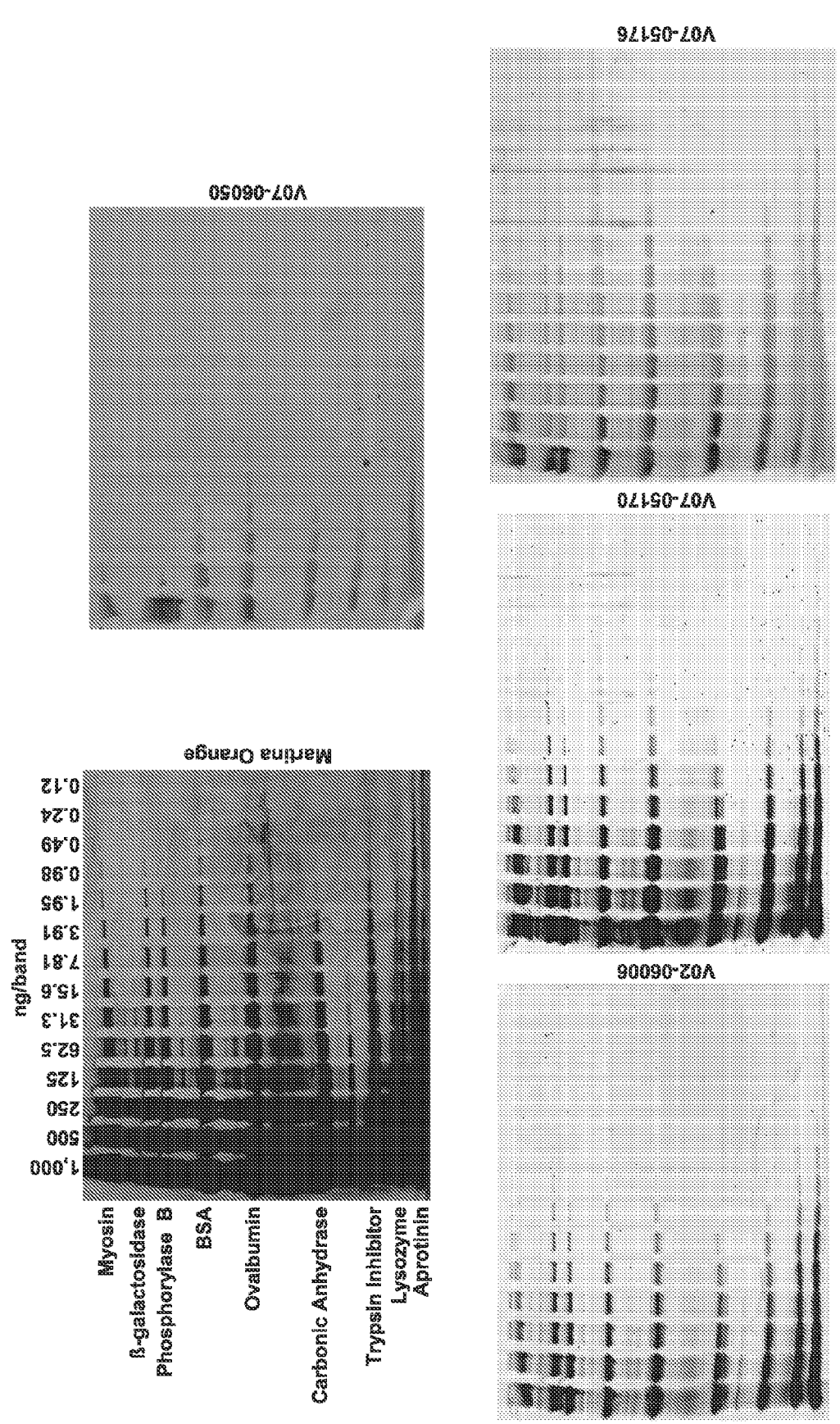
FIG. 3 shows use of coumarine/chinolone and/or Martina-type dyes to stain proteins separated in gels.

Results are shown in FIG. 3. Martina Orange had a sensitivity of 0.12 ng/band with high fluorescent signal and moderate background. V07-06050 had the lowest sensitivity (2 ng/band). V02-06006 and V07-05170 had low background, excellent signal intensity and detected proteins down to about 1 ng/band to about 2 ng/band. V07-05176 had lower fluorescent signal but detected proteins down to about 0.25 ng/band to about 0.5 ng/band.

Protein separation may also occur on a 4-20% Precise Tris-HEPES gel (Pierce), followed by a 20 minute to two hour destain in water, with similar results.

Example 5

Figure 4:
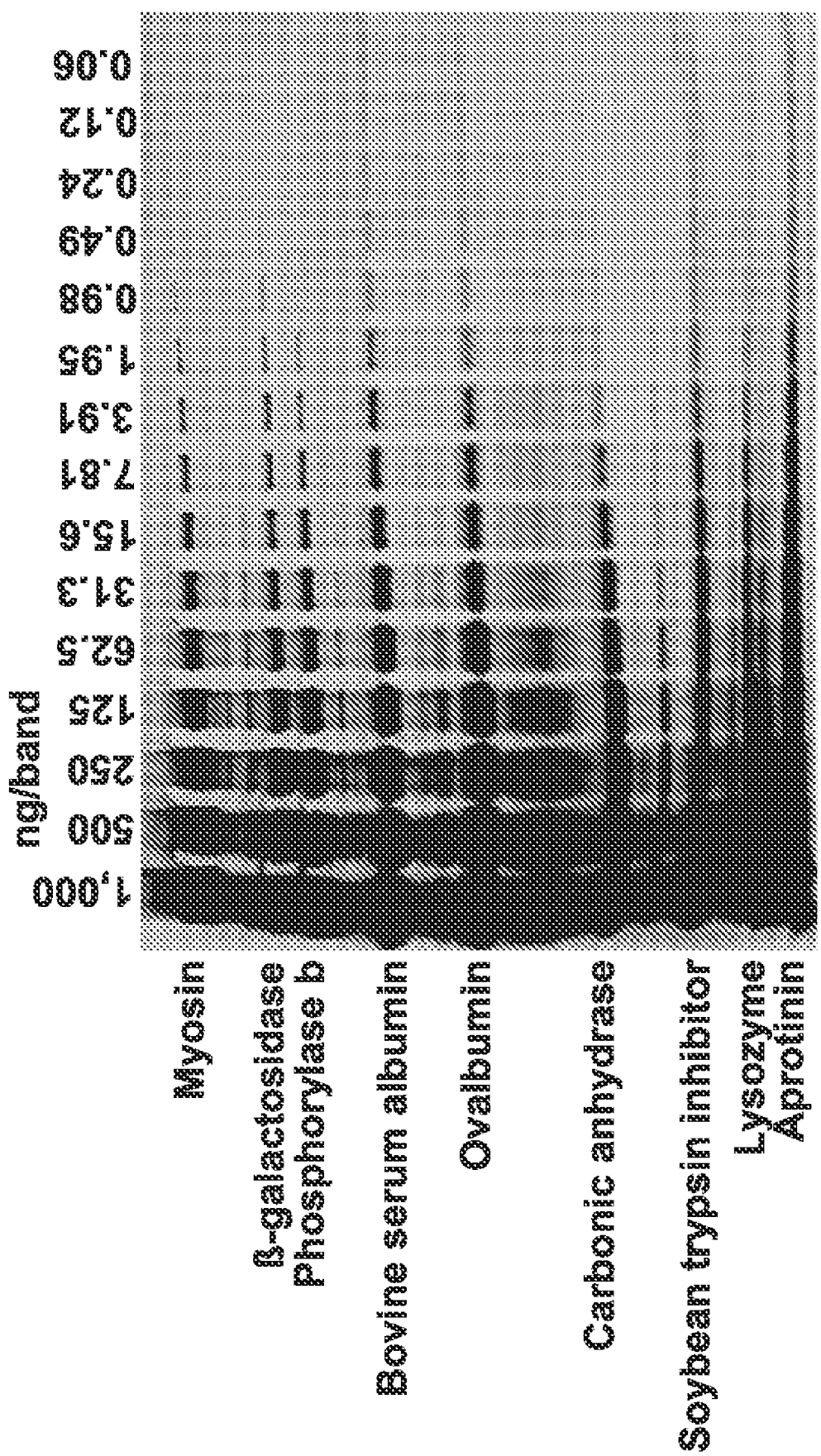
FIG. 4 shows use of Martina-type dyes to stain a broad range molecular weight protein standard separated in a polyacrylamide gel.

The working formulation of the composition may contain one or a combination of more than one of the coumarine/chinolone and/or Martina-type compounds disclosed and/or modified as described, at concentrations ranging from about 25 ng/mL to about 300 ngl/mL. In one embodiment, proteins separated by electrophoresis in a polyacrylamide matrix were stained with a Martina-type compound (Martina Orange) at a concentration of 100 ng/mL in 75 mM sodium propionate, pH 4.0, 50 mM benzaldehyde, 5% (v/v) ethanol, 5% v/v 1,2-propanediol, 0.3% (w/v) polyethylene glycol (PEG). Results are shown in FIG. 4. The proteins were detected down to 0.12 ng per protein band with minimal background.

The dye formulation may contains benzaldehyde at a concentration of at least 50 mM which increases the absorbance and fluorescent intensity, dye stability, dye photostability, and detection sensitivity of coumarine/chinolone and/or Martina-type dyes. Fluorescence is preserved through extended washes. The composition also contains polyethylene glycol (PEG) and/or polyvinyl alcohol (PVA) at 0.1% v/v to about 5% v/v. The PEG and/or PVA reduces background, and thus provides enhanced sensitivity by increasing the signal to noise ratio.

In another embodiment, proteins are stained with any of the compounds alone in a dye composition. In another embodiment, proteins are stained with a mixture of compounds in a due composition (e.g., one red/NIR compound and one Martina-type compound, one red/NIR compound and another red/NIR compound, one Martina-type compound and another Martina-type compound, etc.).

Example 6

The working formulation of the composition may contain one or a combination of more than one of the coumarine/chinolone and/or Martina-type compounds disclosed and/or modified as described, at concentrations ranging from about 25 ng/mL to about 300 ngl/mL. In one embodiment, proteins separated by electrophoresis in a polyacrylamide matrix were stained with a combination of coumarine/chinolone compounds V07-05176 and V02-06006, each at a concentration of 62.5 ng/mL in 100 mM MOPS, pH 6.5, 5% ethanol, and 5% 1,2-propanediol.

Figure 5:
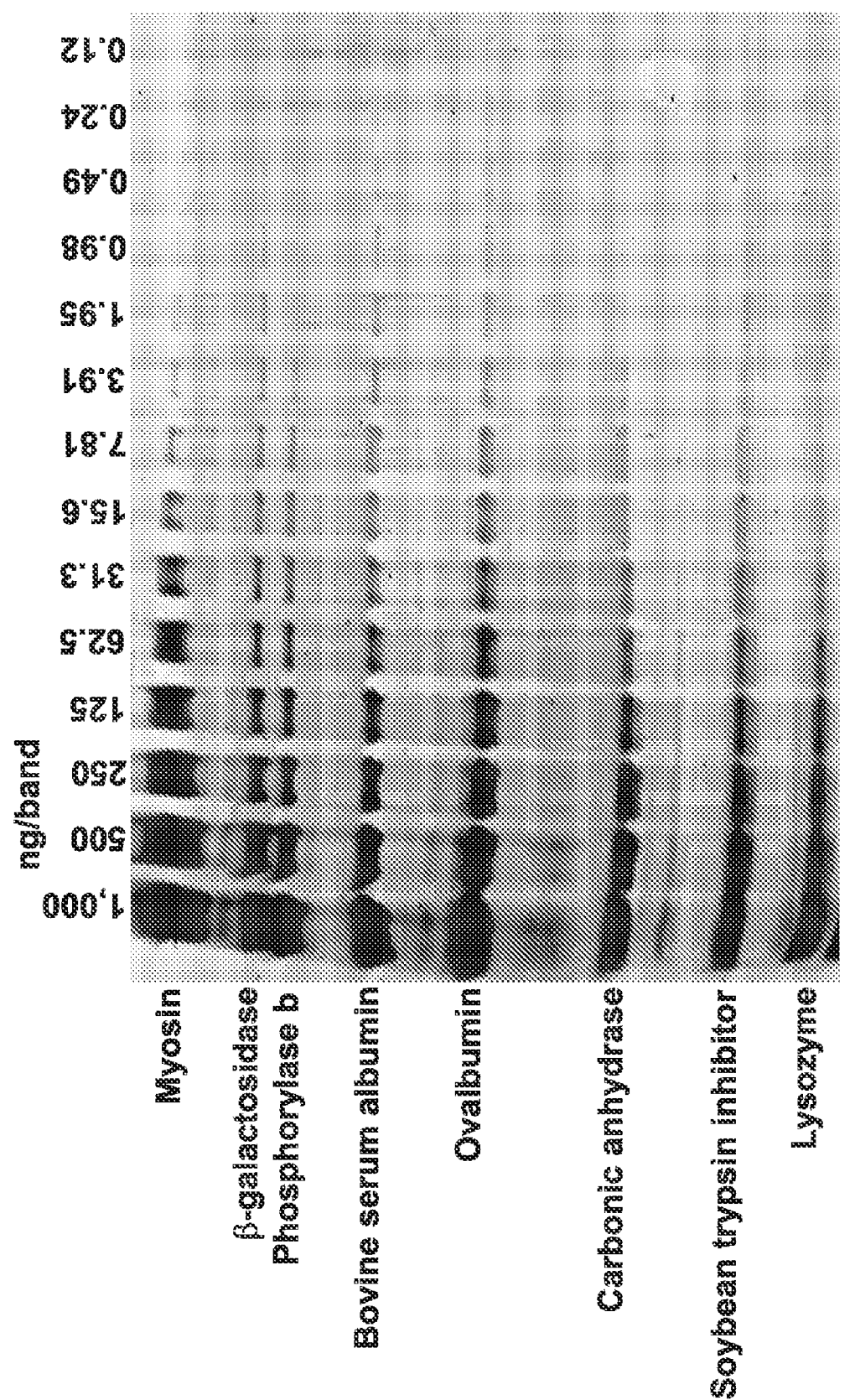
FIG. 5 shows use of coumarine/chinolone dyes to stain a broad range molecular weight protein standard separated in a polyacrylamide gel.

Results are shown in FIG. 5. Proteins are detected down to at least 0.25 ng per protein band with minimal background.

In another embodiment, proteins are stained with any of the compounds alone in a composition. In another embodiment, proteins are stained with any mixture of compounds in the composition, as described in Example 5.

Example 7

A working 1× dye composition is prepared for staining proteins. The proteins may be in a polyacrylamide gel or a solid support, such as nitrocellulose or polyvinylidene fluoride (PVDF) following transfer.

The composition may also be made and stored as a 10× solution. The 10× solution can be stored at about 4° C. to about 25° C. for at least one year. In one embodiment, the 10× solution includes 750 mM sodium propionate, pH 4, 3% w/v polyethylene glycol, 50% v/v 1,2-propanediol, 4.9% v/v ethyl alcohol, 500 mM benzaldehyde, and 1.65 µM coumarine/chinolone and/or Martina-type compound, including modifications of one or more compound(s) as previously described. Before staining proteins, the user dilutes the 10× solution 1 to 10 in water to prepare a 1× working solution that is then used to stain proteins in solution, on gels, membranes, etc.

Example 8

A working 1× dye composition formulation is prepared for staining proteins in a polyacrylamide gel or a solid support, such as nitrocellulose or PVDF, following transfer. The dye formulation may also be made and stored as a 10× solution. The 10× solution can be stored at about 4° C. to about 25° C. for at least one year. In one embodiment, the 10× solution includes 1 M MOPS (3-[N-morpholino]propanesulfonic acid), pH 6.5, 50% v/v 1,2-propanediol, 4.9% v/v ethyl alcohol, and 1.25 µg/mL coumarine/chinolone and/or Martina-type compound, including modifications of one or more compound(s) as previously described.

In one embodiment 625 ng/mL V02-06006 and 625V07-05176 compounds are prepared as a composition. Before staining proteins, the user dilutes the 10× solution 1 to 10 in water to prepare a 1× working solution that is then used to stain proteins in solution, on gels, membranes, etc.

Example 9

Proteins separated by electrophoresis in a gel are stained in about five minutes to about 160 minutes using the disclosed coumarine/chinolone and/or Martina-type compositions. Following electrophoresis, the gels are washed in an alcohol (R—OH) at about 30% v/v to about 50% v/v, and acid (R—CO$_2$) at about 5% v/v to about 15% v/v fixative solution. Examples of alcohols in the fixative solution include methanol, ethanol, and isopropanol. Examples of acids in the fixative solution include formic acid, acetic acid, and proprionic acid. In one embodiment, the fixative solution is about 40% v/v ethanol and about 10% v/v acetic acid. The fixation step can be from about five minutes to overnight.

In one embodiment, fixation involves two consecutive thirty minute incubations in the fixative solution.

In another embodiment, the fixative solution is about 50% ethanol and about 15% acetic acid with two, ten minute incubations in the fixative solution. In another embodiment, the fixative solution is about 15% ethanol, 15% methanol, and 50 mM sodium hydroxide with a thirty minute incubations in the fixative solution.

Following fixation, the gel is washed in water for about five minutes to about fifteen minutes to remove any excess alcohol and/or acid. A 10× dye composition (e.g., 550 mM sodium acetate, pH 4, 3% w/v PEG, 4.9% v/v ethanol, 500 mM benzaldehyde, 50% v/v 1,2-propanediol, and 1.65 µM coumarine/chinolone and/or Martina-type compound(s) or 1 M MOPS, pH 6.5, 50% 1,2-propanediol, 5% ethanol and 625 ng/mL V02-06006 and 625 ng/mL V07-05176, is diluted to a 1× working composition by combining one volume of the 10× composition with nine volumes of water. A sufficient volume of the 1× working composition is used to completely cover the gel. Typically, 20 ml to 35 ml of the composition is sufficient for an 8 cm×10 cm gel. The gel can be stained for a minimum of about five minutes, and may be stained as long as overnight. Longer incubation times in the stain provide greater fluorescent intensity and increase the level of protein detection. In one embodiment, the gel is incubated with the fluorescent protein stain reagent for about one hour to about two hours.

Following staining, the gel is washed with acetic acid at about 5% v/v. The gel is then washed, or destained, in water for a minimum of about three minutes. Extended washing can be used but after about twelve hours, the level of detection decreases. In one embodiment, the destain procedure consists of two consecutive fifteen minute washes in water. In another embodiment the gel is washed with 5% acetic acid and 0.1% Tween-20 for five to fifteen minutes. In another embodiment, the destain wash solution also includes Tween-20 at a concentration less than about 1% v/v. In another embodiment, the gel is destained with a solution of sodium carbonate at a concentration from about 100 mM to about 200 mM, pH about 9 to about 11.

Example 10

The coumarine/chinolone and/or Martina-type dyes can be used to quantitate proteins in solution. Formulations containing various concentrations of the coumarine/chinolone and/or Martina-type dyes, including modifications as previously described, may be added to protein solutions. In one embodiment, one volume of the protein solution is combined with 10 volumes of the dye composition. In another embodiment, one volume of the protein solution is combined with one volume of the dye composition. The resulting protein sample and dye composition may be read immediately or after an incubation period. In one embodiment, the protein sample and dye composition is incubated for about thirty minutes. The assay may be performed in multiple formats, including multiwell microtiter plates, tubes, etc., and read in appropriate fluorometers.

Example 11

Representative gels containing proteins separated by electrophoresis were stained with the compositions containing coumarine/chinolone and/or Martina-type dyes according to methods previously described. For comparison, the following commercial protein standards were used: Broad Range Protein Standards (Bio-Rad), Glycoprotein Standard Mix (Molecular Probes), and Phosphoprotein Mix (Molecular Probes). The protein standards were serially diluted and loaded onto 4-20% Tris-glycine SDS-polyacrylamide gels (Invitrogen) in amounts of 1,000 ng/lane; 500 ng/lane; 250 ng/lane; 125 ng/lane; 62.5 ng/lane; 31.3 ng/lane; 15.6 ng/lane; 7.8 ng/lane; 3.9 ng/lane; 1.95 ng/lane; 0.98 ng/lane, 0.49 ng/lane, 0.24 ng/lane, 0.12 ng/lane, and 0.06 ng/lane. Proteins on all gels were separated by electrophoresis.

Following electrophoresis, gels containing separated proteins were placed in a clean tray and washed two times for ten minutes each with 35 mL 50% v/v ethanol, 15% v/v acetic acid. The gels were then washed for five minutes in water. After the water wash, 35 ml of the 1× stain reagent (100 mM MOPS, pH 6.5; 5% v/v 1,2-propanediol, 0.49% v/v ethanol, and 625 ng/mL V02-06006 and 625 ng/mL V07-05176 were added to the tray containing the washed gel and incubated for one hour with gentle mixing. After staining, the gel was washed with 35 ml 5% v/v acetic acid, 0.1% v/v Tween-20 for five minutes, followed by two consecutive ten minute water washes. The stained gel was imaged on an Odyssey Infrared Imaging System (LI-COR Biosciences) with the 700 nm channel.

Figure 6:
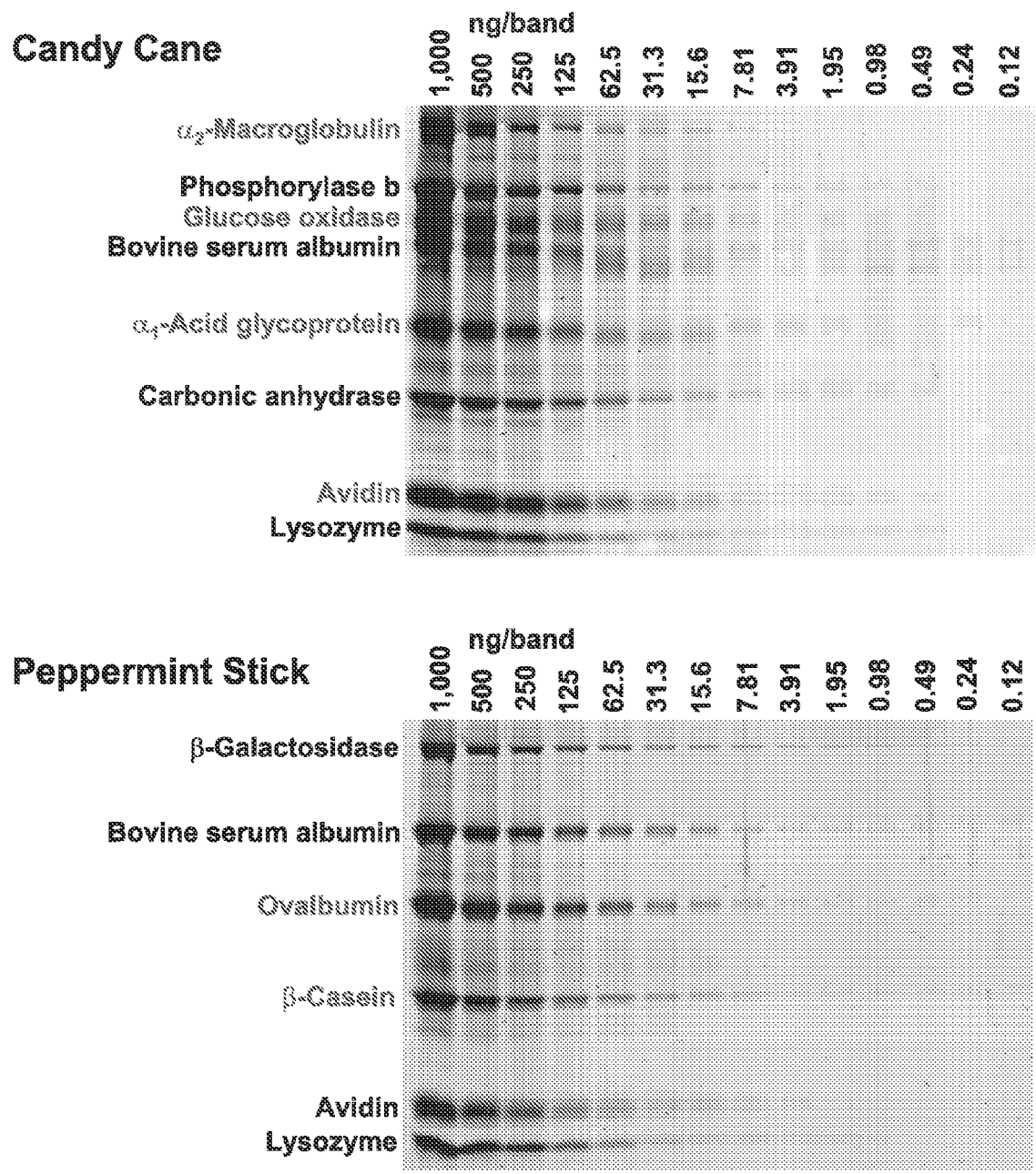
FIG. 6 shows use of coumarine/chinolone and/or Martina-type dyes to stain posttranslationally modified proteins separated in a polyacrylamide gel.

Results are shown in FIG. 6. The stain detected a diverse selection of proteins including phosphoproteins (ovalbumin, β-casein) and glycoproteins ($\alpha_2$-macroglobulin, glucose oxidase, $\alpha_1$-acid glycoprotein, avidin). The detection sensitivity was, at minimum, 1 ng protein per band, but select proteins were detected at a sensitivity of 0.25 ng protein per band. The stain reagent detected most proteins when 0.25 ng protein was loaded onto the gels.

Proteins in a glycoprotein mix are detected at a sensitivity of 1 ng for all proteins, and at a sensitivity of 0.5 ng or less for higher molecular weight proteins such as α-acid glycoprotein. Proteins in a phosphoprotein mix are detected at a sensitivity of 2 ng or less. Variability in detection sensitivity may be a result of slight differences in the protein concentrations of the standards (e.g., a 1% variance in a 1,000 ng protein solution is 10 ng) or due to steric hindrance issues caused by posttranslational modifications such as glycosylation or phosphorylation. These modifications may reduce binding of the dye to the amino acids in the protein.

Example 12

Commercially available HeLa cells and rat heart tissue were lysed (using M-PER, Pierce) and protein content of the lysates is determined by BCA protein assay (Pierce). Lysates were diluted in sample buffer containing SDS and 10 mM DTT to 125 ng total protein/µl (HeLa cell lysates) and 62.5 ng total protein/µl (rat heart tissue). The lysates were serially diluted and 10 µl of each sample is loaded on a 4-20% Tris-glycine SDS gel, and proteins were separated by electrophoresis. Following electrophoresis, gels containing separated proteins were fixed with two, thirty minute washes in 40% ethanol, 10% acetic acid. The gels were then washed for five minutes with water. Working stain reagent (1×) was prepared by diluting the 10× stain reagent (1 M MOPS, pH 6.5, 50% v/v 1,2-propanediol, 4.9% v/v ethanol, and 625 ng/ml V02-06006 and 625 ng/ml V07-05176 1 to 10 in water. The gels were incubated in the 1× working reagent for sixty minutes, washed in 5% acetic acid, 0.1% Tween-20 for five minutes followed by two, ten minutes washes in water, and then stained gels were imaged on an Odyssey Infrared Imaging System (LI-COR Biosciences) at the 700 nm channel.

The protein profile of the lysates was observed as a smear, with high abundant proteins appearing as distinct bands (data not shown). The distinct protein bands were detected at a sensitivity of 39 ng total protein/well or less with the HeLa cell lysate, and 20 ng total protein/well or less with the rat heart tissue cytosolic extract (data not shown).

Example 13

HeLa cell lysates were prepared as described in Example 12 and equilibrated in 8 M urea, 4% CHAPS using a 2-D Sample Prep for Soluble Proteins (Pierce, #89865). Lysate protein (28 µg), determined by BCA Assay (Pierce #23225), was separated using pH 5-8 IPG strips (Bio-Rad) for isoelectric focusing for the first dimension, and SDS-PAGE on 4-20% Tris-HCl gels (Bio-Rad) for the second dimension. The gels were stained according to previously described protocol using coumarine/chinolone and/or Martina-type compounds formulated as a dye composition, and stained gels were imaged using an Odyssey Infrared Imaging System 9LI-COR Biosciences) at the 700 nm channel.

Figure 7:
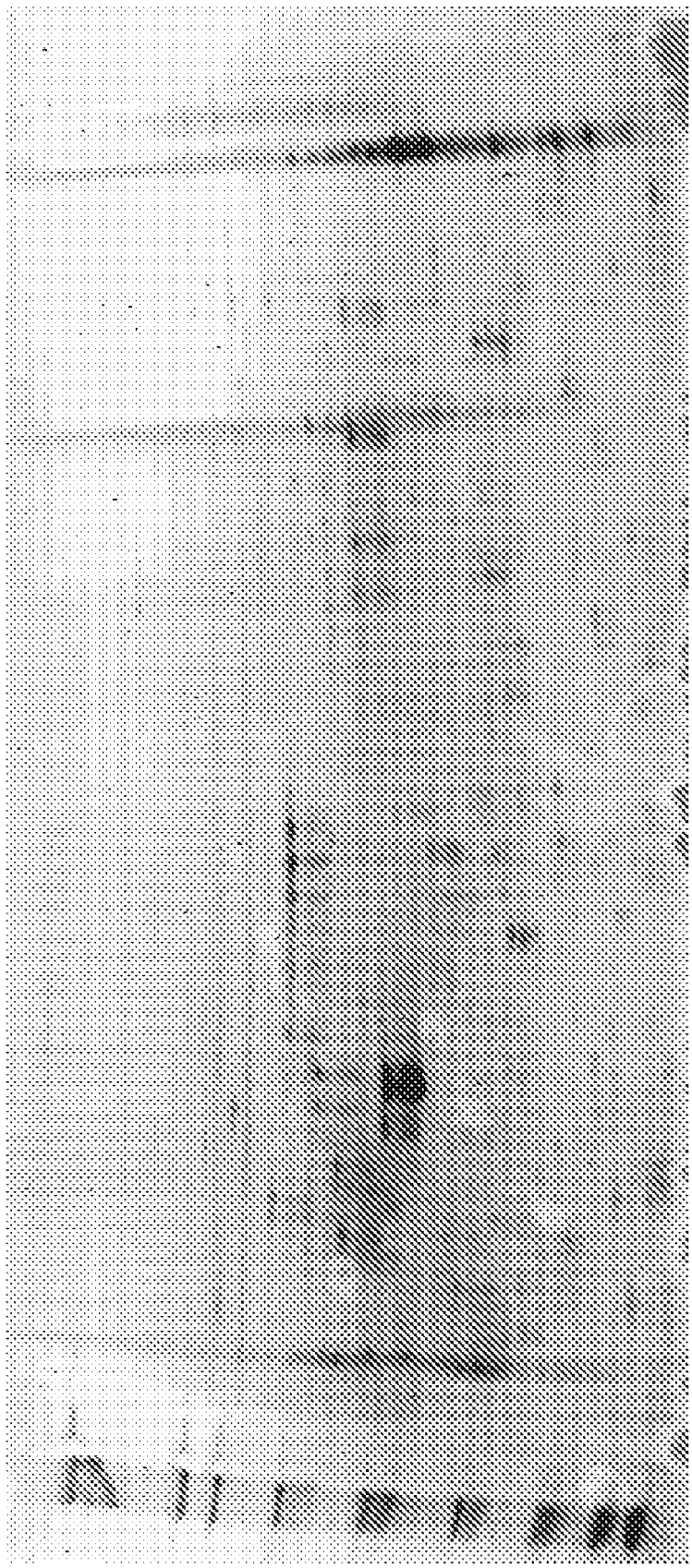
FIG. 7 shows use of coumarine/chinolone and/or Martina-type dyes to detect proteins separated on gels by two dimensional electrophoresis.

Results are shown in FIG. 7. The coumarine/chinolone and/or Martina-type compositions stain protein mixtures separated in two dimensions providing sharp, intense detection of proteins, with minimal protein-to-protein variability and a wide range of detection.

Example 14

To determine the extent of linearity of protein standard curves using a representative compound in the fluorescent protein stain composition, selected proteins available as commercial protein standards are serially diluted. Each protein set is separated by electrophoresis on either Novex 4-20% Tris-glycine SDS gels (Invitrogen) or Criterion 4-20% Tris-HCl SDS gels (Bio-Rad) creating a concentration gradient of protein bands. Gels containing separated proteins are stained with the fluorescent protein stain reagent containing a coumarine/chinolone and/or Martina-type dye and imaged on an Odyssey Infrared Imaging System (LI-COR Biosciences) at the 700 nm channel.

The relative fluorescent intensity of the separated protein bands is determined using Odyssey software. The log of the relative intensity is plotted versus the log of the protein band concentration. The best fit line is determined by linear regression and the $R^2$ value is indicated for each line. Myosin and bovine serum albumin are examples of high molecular weight proteins, β-casein an example of a phosphoprotein, α-acid glycoprotein an example of a glycoprotein, and lysozyme and trypsin inhibitor are examples of low molecular weight proteins.

Figure 8:
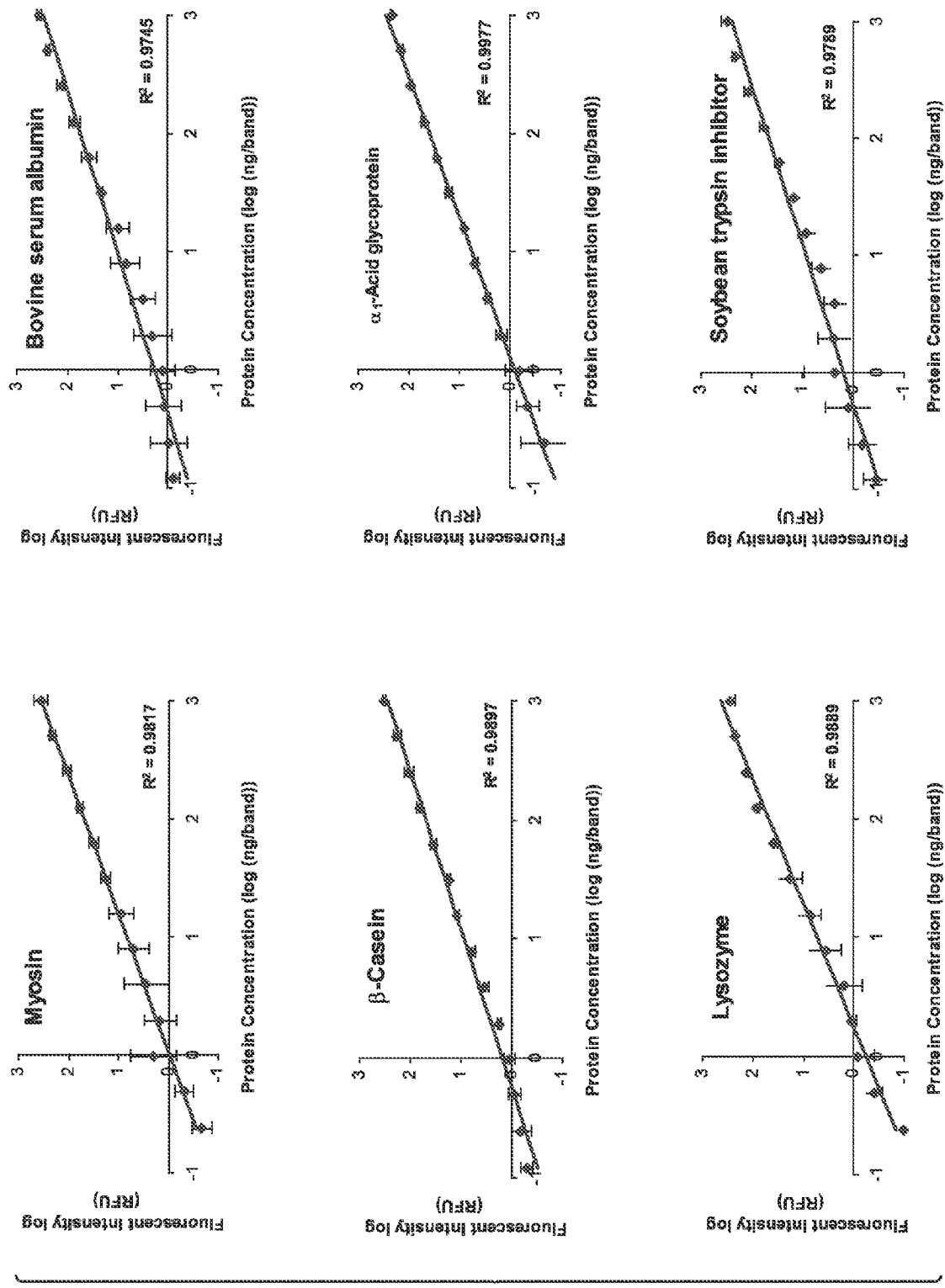
FIG. 8 graphs fluorescent output using a coumarine/chinolone dye versus protein concentration using high and low molecular weight proteins.

The linear quantification range of all proteins stained with the fluorescent protein stain reagent extends over several orders of magnitude (FIG. 8). Myosin, bovine serum albumin, β-casein, α-acid glycoprotein, lysozyme and trypsin inhibitor may be quantified over three to four orders of magnitude.

Example 15

The fluorescent protein stain reagent was reversible and compatible with MALDI-MS analysis.

Bovine serum albumin (100 ng) or horse heart myoglobin (200 ng) was loaded on 4-20% Tris glycine gels and separated by electrophoresis. Gels containing the separated proteins were stained using a representative compound as the fluorescent protein stain reagent (100 mM MOPS, pH 6.54, 4.9% ethanol, 5% 1,2-propanediol, 62.5 ng/ml V02-06006 and 62.5 ng/ml V07-05176.

Bands containing separated proteins were excised from gels as gel plugs, protein was digested with trypsin, and the peptide fragment digests were extracted using methods known to one skilled in the art. The resulting peptide fragments were further purified with ZipTips (Milli Pore) and spotted for MALDI-MS analysis in matrix (2 mg/ml α-cyano-4-hydroxycinnamic acid, 50% acetonitrile, and 0.1% trifluoroacetic acid).

Figure 9:
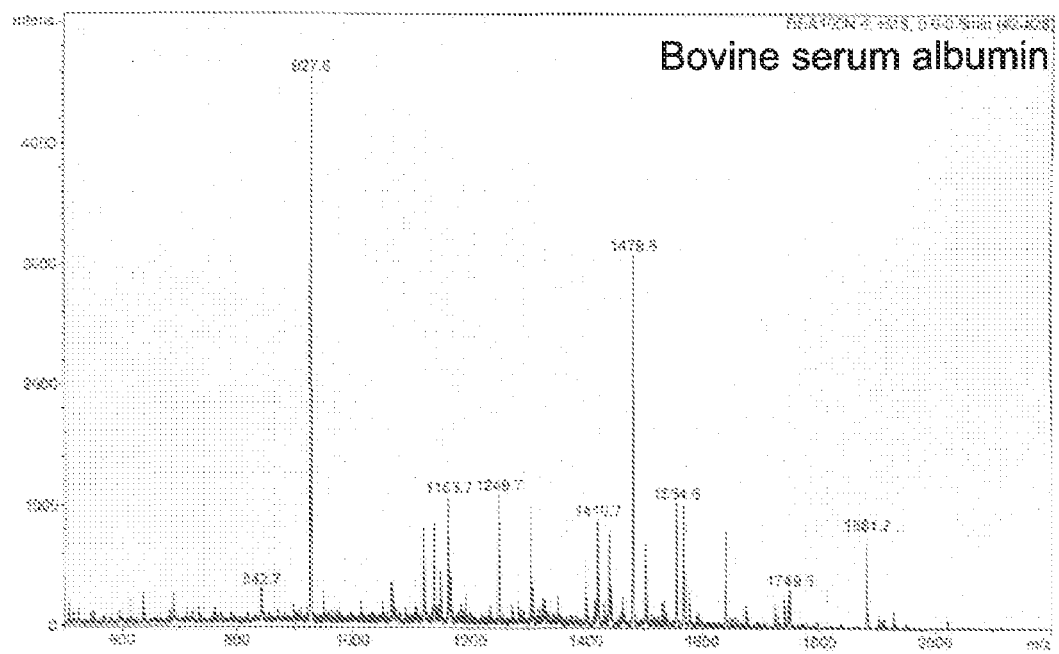
FIG. 9 shows matrix-assisted laser desorption/ionization mass spectra (MALDI-MS) of proteins stained by coumarine/chinolone dyes.
Figure 9:
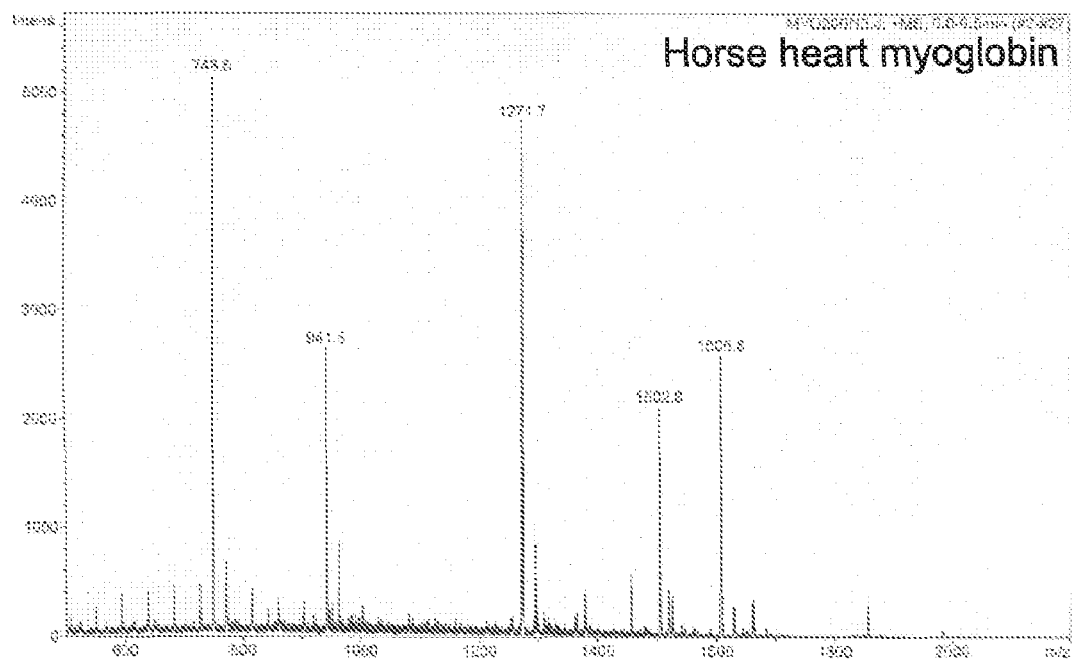

Characteristic peaks were observed for digests from bovine serum albumin and myoglobin stained as described (FIG. 9). The mass peaks corresponded to the tryptic peptide fragments and did not exhibit any mass increase that would be representative of the dye mass or modification of the protein.

Example 16

The dye composition reagent detected a broad range of proteins using multiple polyacrylamide gel formats. Serial dilutions of commercially available protein standards, previously described, were separated by electrophoresis on the following gels: Criterion 4-20% Tris-HCl (Bio-Rad); Precise 4-20% Tris-HEPES (Pierce); and 12% NuPage gel, MOPS buffer (Invitrogen).

Figure 10:
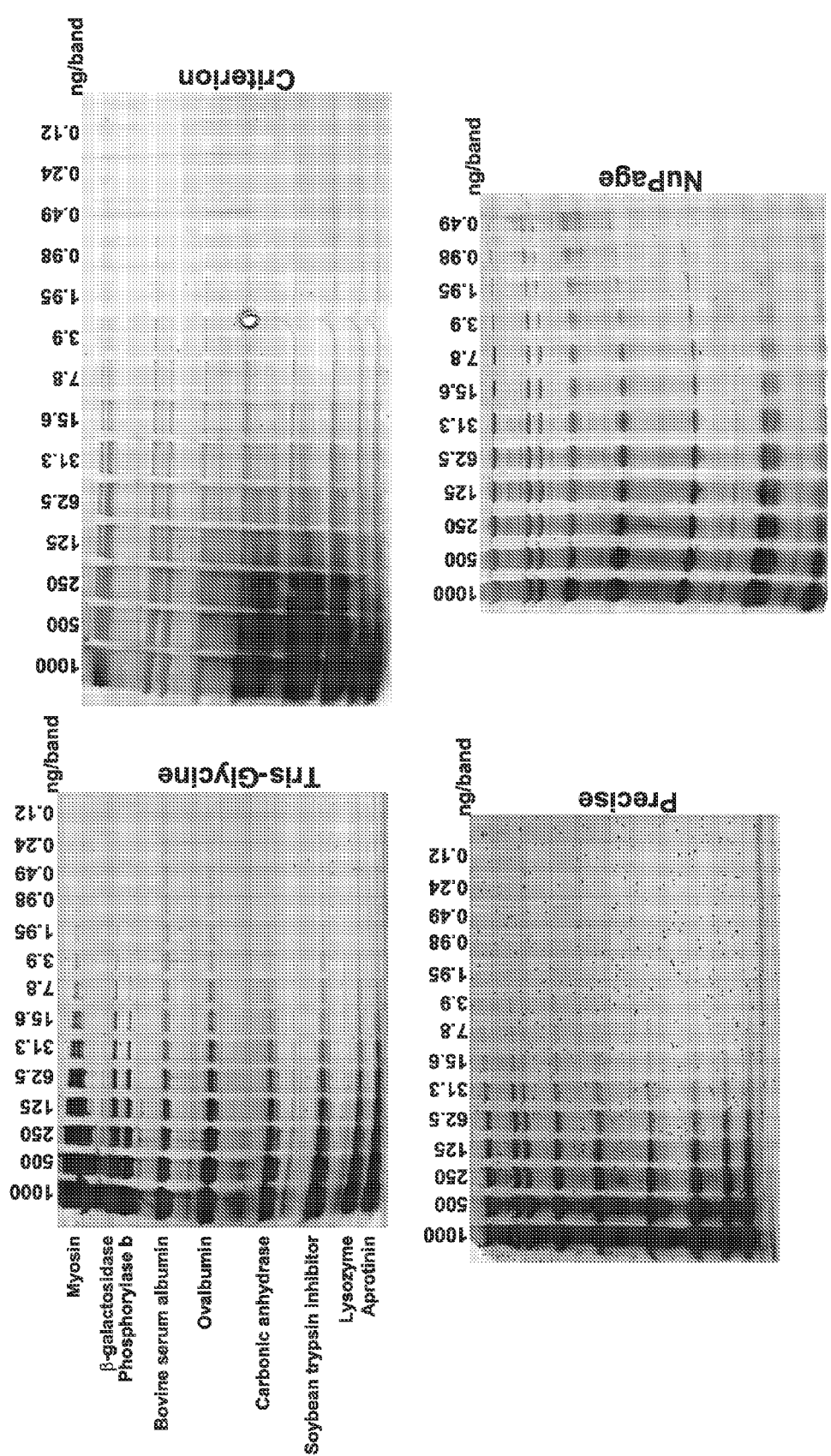
FIG. 10 shows use of coumarine/chinolone and/or Martina-type dyes to detect a broad range of proteins separated on multiple polyacrylamide gel formats.

Results are shown in FIG. 10. Gels containing separated proteins were stained with the fluorescent protein stain reagent containing a coumarine/chinolone and/or Martina-type compound provided equivalent or superior protein staining and detection in less time compared to existing fluorescent stains using multiple gel formats.

Example 17

The dye composition was selective for proteins over nucleic acids. Two 6% polyacrylamide DNA retardation gels were loaded with a 100 bp DNA ladder and a broad range protein standard. Electrophoresis was performed in 0.5× tris borate EDTA (TBE) running buffer at pH 8.3.

One gel containing separated proteins and nucleic acids was stained with ethidium bromide and visualized on a Typhoon 9410 Variable Mode Imager (GE Healthcare) using 532 nm laser, 610 BP 30 emission filter and a PMT setting of 400 V. This gel served as the positive control, indicating the presence of DNA in the gel.

The other gel containing separated proteins and nucleic acids was stained with the 1× coumarine/chinolone and/or Martina-type stain reagent and was imaged on an Odyssey Infrared Imaging System (LI-COR Biosciences) at the 700 nm channel.

Figure 11:
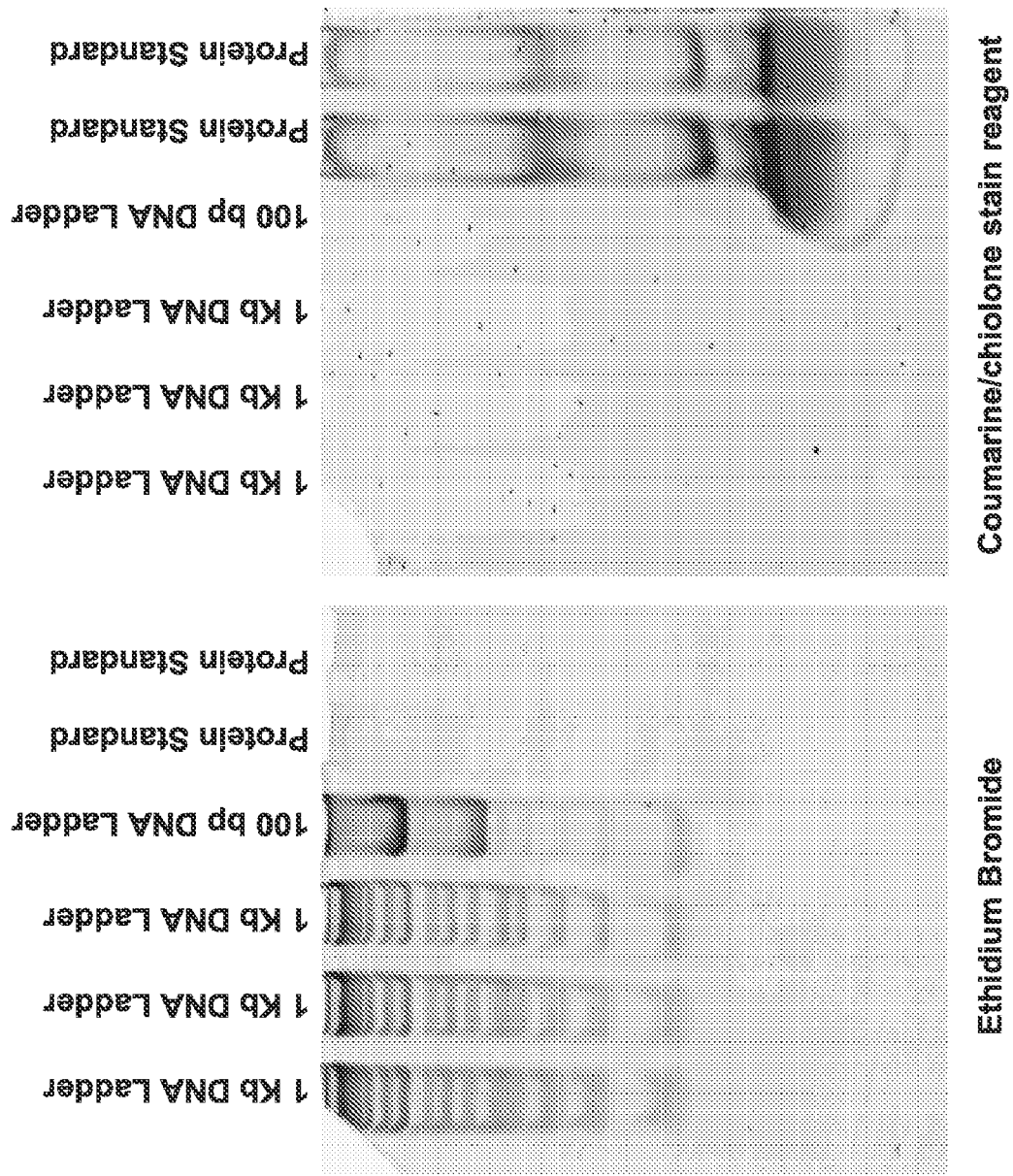
FIG. 11 shows gels on which protein and nucleic acid were separated and stained by ethidium bromide and coumarine/chinolone dye.

Results are shown in FIG. 11. The fluorescent protein stain reagent detected the protein standard but did not detect the DNA ladder. The results indicated that the coumarine/chinolone and/or Martina-type stain was specific for amino acids and proteins.

Example 18

The dye composition is compatible with multiple imaging platforms, including but not limited to a CCD imager, a laser based scanner, and a UV transilluminator.

Protein standards are separated by electrophoresis in a 4-20% Tris-glycine gel and stained with either 62.5 ng/mL of V07-05176 and 62.5 ng/mL of V02-06006 in 100 mM MOPS, pH 6.5, 5% ethanol, and 5% 1,2-propanediol or Martina Orange at 100 ng/mL in 75 mM sodium propionate, pH 4.0, 50 mM benzaldehyde, 5% v/v ethanol, 5% v/v 1,2-propanediol, 0.3% w/v polyethylene glycol (PEG)). The gel containing separated proteins is imaged on a Kodak 200 mm Imager using a 625 nm to 680 nm excitation filter, 700 nm to 720 nm emission filter with a five minute exposure, and an Odyssey Infrared Imaging System (LI-COR Biosciences) at the 700 nm channel for infrared spectra. The gel containing separated proteins is imaged on a Kodak 200 mm Imager using a 535 nm excitation filter, 600 nm emission filter with a five minute exposure, and a Typhoon 9410 Variable Mode Imager (GE Healthcare) using 532 nm laser, 580 BP 30 emission filter and a PMT setting of 600 V for visible spectra. Protein bands are detected at a sensitivity of 1.95 ng or less when staining with the dye composition and imaging with either a CCD or laser based imaging platform.

Example 19

A coumarine/chinolone and/or Martina-type compound was dissolved in dimethylformamide (DMF) at 1 mg/ml and diluted to 10 μg/ml, 5 μg/ml, and 2.5 μg/ml in water. One hundred and fifty μl of each dilution was added to four separate wells of a 96-well black microtiter plate. To one well containing each of these dilutions of the assay reagent, 25 μl of bovine serum albumin (prepared in 150 mM NaCl/0.02% sodium azide solution) was added at 2 mg/ml, 1 mg/ml, and 0.5 mg/ml respectively.

Figure 12:
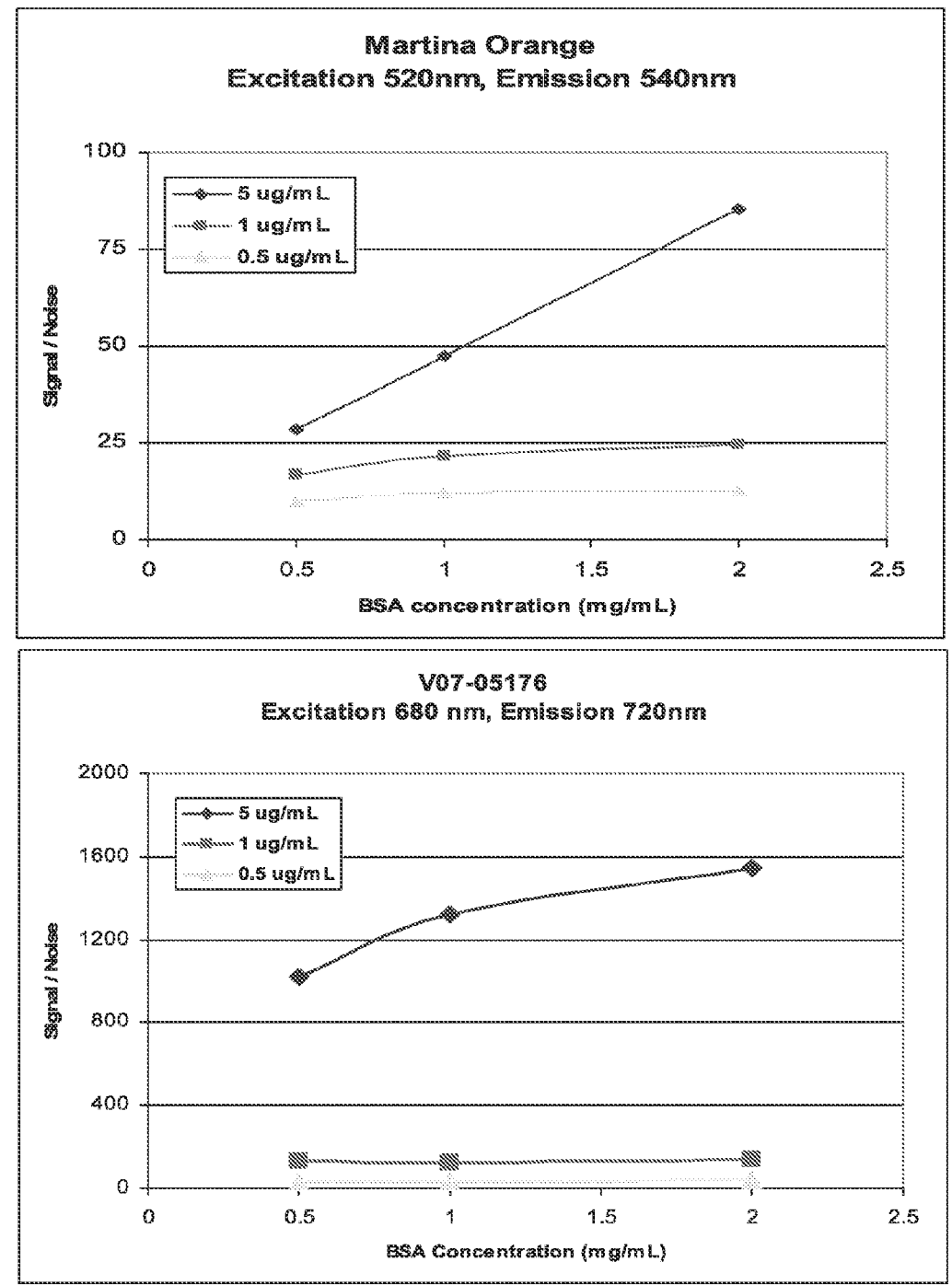
FIG. 12 shows use of coumarine/chinolone and/or Martina-type dyes for detecting proteins in solution in a multiwell format.

In one embodiment using Martina Orange, the plate was read immediately using the Tecan Saffire instrument at 520 nm excitation and 540 nm emission with a gain of 66 for Martina Orange. The compound exhibited increasing signal to noise (S/N) ratio with increasing protein concentration (FIG. 12). In one embodiment, 5 μg/ml dye had the best differential response to increasing protein concentration.

In another embodiment using V07-05176, the plate was read immediately using the Tecan Saffire instrument at 680 nm excitation and 720 nm emission with a gain of 96 for V07-05176. The compound exhibited increasing signal to noise (S/N) ratio with increasing protein concentration (FIG. 12). In one embodiment, 5 μg/ml dye had the best differential response to increasing protein concentration.

The above examples 1-19 and descriptions demonstrated that the dye composition stained a diverse set of proteins such as phosphoproteins, glycoproteins, and proteins derived from cell lysates. Staining was compatible with proteins separated by electrophoresis on both one- and twp-dimensional gels and proteins in solution. It permitted protein quantitation over four orders of magnitude, and linear quantitation over at least three and, for some proteins, of at least four orders of magnitude. The dye composition allowed detection to less than 0.25 ng protein, based on a broad range of proteins in one-dimensional gels. The dye composition selectively stained proteins over nucleic acids, and was compatible with MALDI-MS analysis, and multiple gel types and imaging platforms Example 20

The compound is modified with at least one chelating group, e.g., a metal such as copper. A composition containing the chelated compound is diluted to optimize its use for total protein assay or total protein detection. The composition is then incubated with a protein and protein standards along with a blank. For in-solution assays, the samples are read using a fluorimeter. For assays of proteins on a membrane or in a gel, detection is by a laser-based imager or a CCD camera fitted with appropriate filters. For proteins immobilized on or in a solid support, such as membranes or gels, a pre-treatment step may be required before incubation with the composition. Pretreatment includes, but is not limited to, a fixation step in an alcohol with either a base or acid, blocking reagents such as PEG or PVA, etc. A wash step may be required after the incubation step.

Example 21

The compound is modified with at least one chelating group, e.g., a metal such as cobalt or nickel (for histidine binding) or gallium or iron (for phophoprotein binding). A composition containing the chelated compound is diluted to optimize specific detection of the tagged protein. The composition is then incubated with the protein of interest. For in-solution assays, the samples are read using a fluorimeter. For assays of proteins on a membrane or in a gel, detection is by a laser-based imager or a CCD camera fitted with appropriate filters. For proteins immobilized on or in a solid support, such as membranes or gels, a pre-treatment step as described in Example 20 may be required before incubation with the dye formulation and a wash step may be required after the incubation step.

Example 22

The compound is modified with a hydrazide. A composition is prepared in an organic solvent and is diluted in a buffer formulation to optimize selective binding to carbohydrates. The formulation may include the hydrazide-activated fluorescent dye (e.g., about 0.1 mM to about 5 mM) in a buffer such about 50 mM to about 100 mM sodium acetate, pH 5.5, 5% v/v ethanol, 5% v/v 1,2-propanediol, 0.3% w/v polyethylene glycol (PEG).

The composition is then allowed to bind to the proteins/glycoproteins in solution or on or in a solid support such as a gel. For in-solution assays, the sample is incubated for 30 minutes with about 1 mM to about 20 mM sodium periodate (final concentration sodium periodate). The oxidized sample is desalted or dialyzed and then incubated with the hydrazide-activated fluorescent dye formulation escribed above for about one to two hours. Change in fluorescence is determined using a fluorimeter.

For proteins immobilized on or in a solid support, such as membranes or a gel, a pre-treatment step as described in Example 20 may be required before incubation with the dye formulation. The support is incubated with about 1 mM to about 20 mM sodium periodate for about thirty to about sixty minutes. The support is washed 3×10 minutes with a buffer such as about 50 mM to about 100 mM sodium acetate, pH 5.5, and then incubated with the hydrazide-activated fluorescent dye formulation described above for about one to two hours. The support is then washed 3×10 minutes with phosphate buffered saline (PBS; pH 7.2) containing 0.05% Tween 20. The support is then imaged with a laser imager or CCD camera fitted with appropriate filters.

Example 23

The compound is modified with a maleimide or iodoacetyl group. A composition is prepared in an organic solvent and then diluted to optimize selective binding to sulfhydryls.

The composition is then allowed to bind to the proteins under reducing or non-reducing conditions, either in-solution or on or in a solid support such as a membrane or gel. For in-solution assays, the sample is incubated with iodoacetyl- or maleimide-activated fluorescent compound (final concentration about 0.1 mM to about 5 mM) in buffer (e.g., sodium phosphate, 100 mM pH 6.5 to pH 7.5, containing 5% v/v ethanol, 5% v/v 1,2-propanediol, 0.3% w/v polyethylene glycol. After about thirty to about sixty minutes incubation, the sample is read using a fluorimeter.

For proteins immobilized on or in a solid support, such as membranes or a gel, a pre-treatment step as described in Example 20 may be required before incubation with the dye formulation. The support is washed 3×10 minutes with a buffer such as 100 mM sodium phosphate, pH 6.9 and then incubated with the maleimide- or iodoacetyl-activated fluorescent compound containing formulation described above for about one to about two hours. The support is then washed 3×10 minutes with phosphate buffered saline (PBS; pH 7.2) containing 0.05% Tween 20. The support is then imaged with a laser imager or CCD camera fitted with appropriate filters Example 24

Compounds that are rendered reactive may be conjugated to macromolecules, such as protein (e.g., antibodies, Streptavidin) and used in immunofluorescence assays (e.g. Western blot, ELISA, flow cytometry, in-cell assays, etc. Reactive dyes conjugated to oligonucleotides may be used in hybridization assays, Northern blots, Southern blots, etc.

Other variations or embodiments will also be apparent to one of ordinary skill in the art from the above figures, description, and examples. Thus, the forgoing embodiments are not to be construed as limiting the scope of the following claims.

What is claimed is:

1. A method for staining at least one protein, the method comprising providing a dye comprising compounds V07-05176

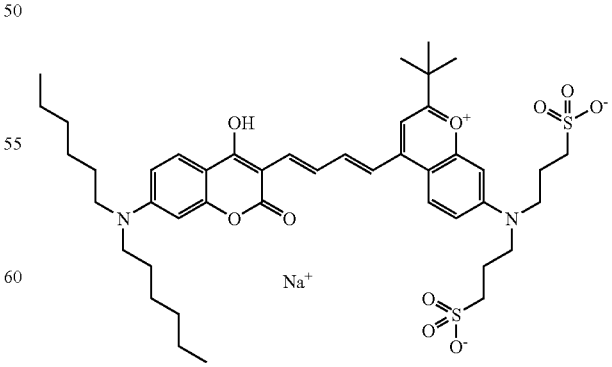

V07-05176

V02-06006

-continued

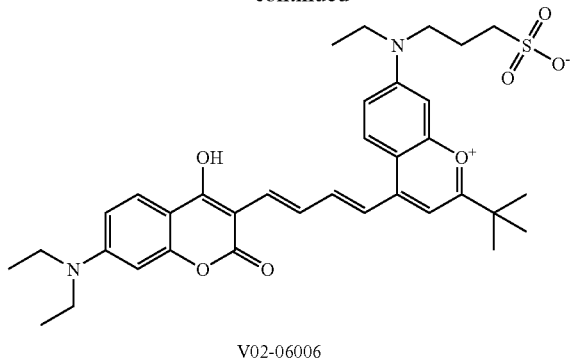

V02-06006 and at least one biocompatible excipient to at least one protein to form a dye-protein complex to stain the protein.

2. The method of claim 1 wherein at least one of compound V07-05176 or compound V02-06006 is in the form of a dye-chelate complex.

3. The method of claim 1 wherein a chelating agent of the dye-chelate complex is selected from the group consisting of iminodiacetic acid, nitrilotriacetic acid, 1,2 bis(o-aminophenoxylethane N,N,N'N' tetraacetic acid, diimines, and combinations thereof, and wherein the chelating agent is chelated to a metal.

4. The method of claim 2 wherein the dye-chelate complex results in increased detergent compatibility.

5. The method of claim 1 wherein the compound further contains a group reactive with at least one of a primary amine, sulfhydryl, carbohydrate, or hydroxyl.

6. The method of claim 5 wherein the group is selected from at least one of hydroxysuccinimide, maleimide, iodoacetamide, hydrazide, or phenyl azide.

7. The method of claim 5 wherein one protein stained is one a protein assay, immunofluorescence assay, singleplex application for protein-protein interactions, or multiplex application for protein-protein interactions.

8. The method of claim 5 wherein one protein stained is one in a multiplex application in combination with other fluorescent dyes or conjugates.

9. A biocompatible composition comprising compounds V02-06006, V07-05176, and at least one biocompatible excipient, where V02-06006 is and V07-05176 is

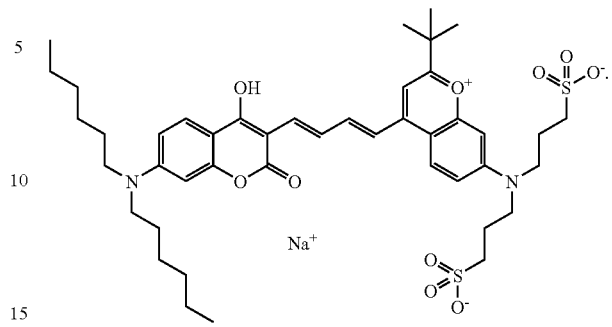

10. The method of claim 1 wherein protein detection sensitivity exceeds 3 ng protein.

11. The method of claim 1 wherein protein detection sensitivity exceeds 0.25 ng protein.

12. A biocompatible dye composition comprising at least one excipient and a compound selected from the group consisting of compounds V02-06006, V07-05176, and combinations thereof, in a concentration ranging from about 25 nmol/L to about 500 mmol/L, where compound V02-06006 is

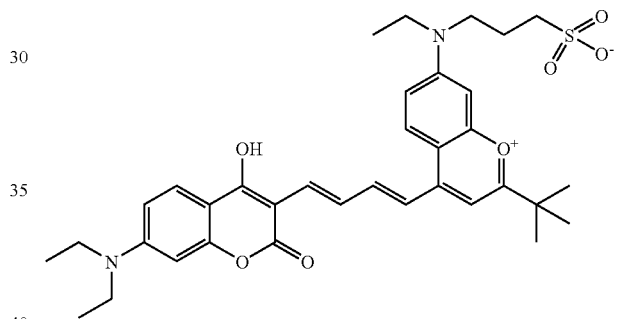

and compound V07-05176 is

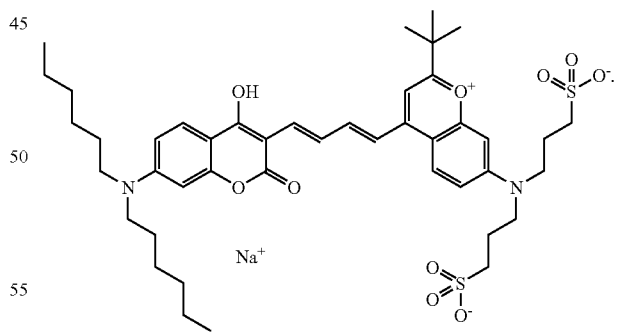

13. A method of staining at least one protein, the method comprising
providing a composition comprising at least one excipient and a compound selected from the group consisting of compounds V02-06006, V07-05176, and combinations thereof in an effective concentration to a protein under conditions sufficient for binding the compound to the protein, and
detecting the protein-bound compound, where compound V02-06006 is
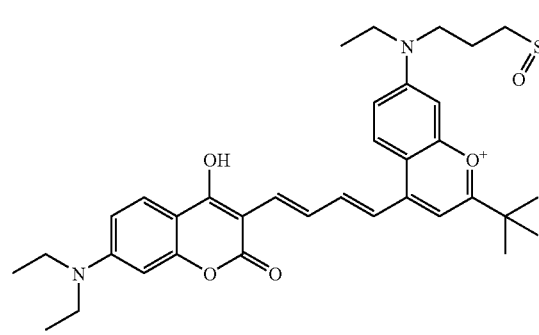
and compound V07-05176 is
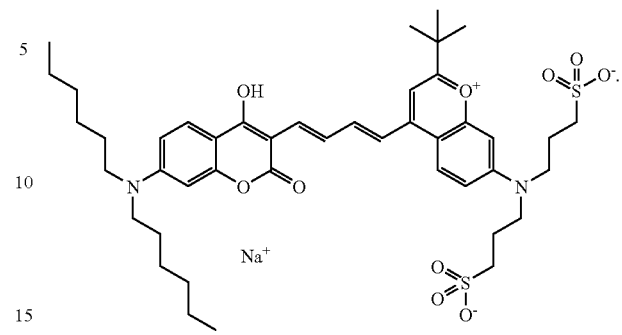
* * * * *

UNITED STATES PATENT AND TRADEMARK OFFICE
CERTIFICATE OF CORRECTION

PATENT NO. : 7,553,869 B2  Page 1 of 1
APPLICATION NO. : 11/460700
DATED : June 30, 2009
INVENTOR(S) : Peter T. Czerney et al.

It is certified that error appears in the above-identified patent and that said Letters Patent is hereby corrected as shown below:

Claim 3, Col. 33, Line 24: "1" should read --2--

Claim 7, Col. 33, Line 41: Insert --in-- before "a protein"

Signed and Sealed this

Seventeenth Day of November, 2009

David J. Kappos
*Director of the United States Patent and Trademark Office*